United States Patent [19]

Matsuo et al.

[11] Patent Number: 5,369,107

[45] Date of Patent: Nov. 29, 1994

[54] THIAZOLE DERIVATIVES, PROCESSES FOR PRODUCTION THEREOF AND PHARMACEUTICAL COMPOSITIONS COMPRISING THE SAME

[75] Inventors: Masaaki Matsuo, Toyonaka; Takashi Ogino, Kobe; Norihiro Igari, Amagasaki; Hachiro Seno, Kadoma; Kyoichi Shimomura, Suita, all of Japan

[73] Assignee: Fujisawa Pharmaceutical Co., Ltd., Osaka, Japan

[21] Appl. No.: 90,325

[22] Filed: Jul. 13, 1993

Related U.S. Application Data

[60] Division of Ser. No. 867,085, Apr. 14, 1992, Pat. No. 5,256,675, which is a continuation of Ser. No. 554,413, Jul. 19, 1990, abandoned.

[30] Foreign Application Priority Data

Aug. 7, 1989 [GB] United Kingdom ............ 8918045.9
Feb. 21, 1990 [GB] United Kingdom ............ 9003930.6

[51] Int. Cl.$^5$ .................. A61K 31/505; A61K 31/44; A61K 31/41; A61K 31/425
[52] U.S. Cl. ..................... 514/252; 514/274; 514/336; 514/362; 514/363; 514/369; 544/316; 544/319; 544/405; 546/280; 548/135; 548/184; 548/185
[58] Field of Search ............ 544/316, 319, 405; 546/280; 548/184, 185, 135; 514/252, 274, 336, 342, 363, 369

[56] References Cited

U.S. PATENT DOCUMENTS 4,649,146  3/1987  Takaya et al. .
4,735,957  4/1988  Takaya et al. .
4,921,887  5/1990  Matsuo et al. .
5,256,675  10/1993  Matsuo et al. .

OTHER PUBLICATIONS

Gibbs et al., "Sulfur Derivatives of Thiazoles" Chemical Society Journal, (1945) pp. 925–926.
Claub et al., "β-Lactame mit über Heteroatomegebundenen Substituenten" (1974) Liebigs Annalen Chemi., 539.
M. Ohta et al., Chemical Abstracts 45:7111g (1951).

Primary Examiner—Mukund J. Shaw
Assistant Examiner—Matthew V. Grumbling
Attorney, Agent, or Firm—Oblon, Spivak, McClelland, Maier & Neustadt

[57] ABSTRACT

Compounds of the formula:

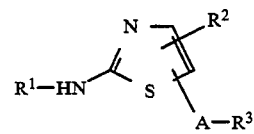

wherein A is S, SO, or SO2, R1 is H or acyl, R2 is H, alkyl, hydroxyalkyl, halogen or carboxy, and R3 is pyridyl are claimed. The compounds are useful as therapeutic agents for the treatment of e.g. rheumatism, nephritis and thrombocytopenia.

4 Claims, No Drawings

THIAZOLE DERIVATIVES, PROCESSES FOR PRODUCTION THEREOF AND PHARMACEUTICAL COMPOSITIONS COMPRISING THE SAME

This is a divisional of application Ser. No. 07/867,085, filed Apr. 14, 1992, U.S. Pat. No. 5,256,675, which is a continuation of application Ser. No. 07/554,314, filed Jul. 19, 1990, abandoned.

This invention relates to new thiazole derivatives.

More particularly, this invention relates to new thiazole derivatives and pharmaceutically acceptable salts thereof which have pharmacological activities, processes for production thereof, pharmaceutical compositions comprising the same and methods of use thereof.

Accordingly, one object of this invention is to provide new and useful thiazole derivatives and pharmaceutically acceptable salt thereof.

Another object of this invention is to provide processes for production of said thiazole derivatives and pharmaceutically acceptable salts thereof.

A further object of this invention is to provide pharmaceutical compositions comprising said thiazole derivatives of pharmaceutically acceptable salts thereof.

A still further object of this invention is to provide methods of using said tniazole derivatives or pharmaceutically acceptable salts thereof for therapeutic treatment of rheumatism, nephritis, thromaocytopenia, tumor or side effect of an antitumor agent in human being and animals.

The object thiazole derivatives of this invention are novel and represented by the following general formula (I):

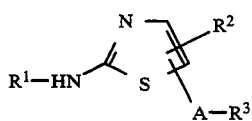

wherein
R$^1$ is hydrogen or acyl which may be substituted with halogen,
R$^2$ is hydrogen, lower alkyl, hydroxy(lower)alkyl, halogen or carboxy,
A is —CH$_2$—, —CO—, —C(=NOR$^4$)— wherein R$^4$ is lower alkyl],

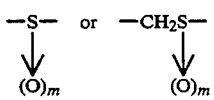

[wherein m is 0, 1 or 2], and
R$^3$ is aryl which may be substituted with halogen, hydroxy, lower alkoxy, nitro, amino or acylamino; or N-containing unsaturated heterocyclic group which may be substituted with lower alkyl, amino, hydroxy or hato(lower)alkyl.

The object compound (I) of the present invention can be prepared by the following processes.

Process 1

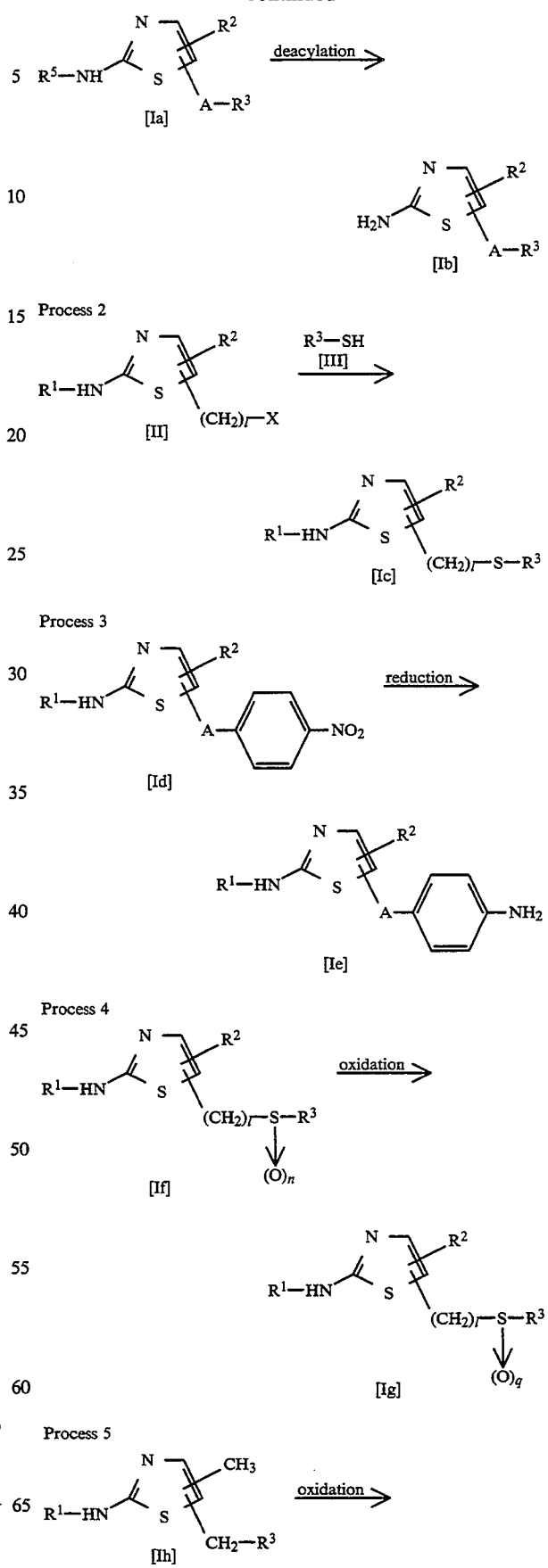

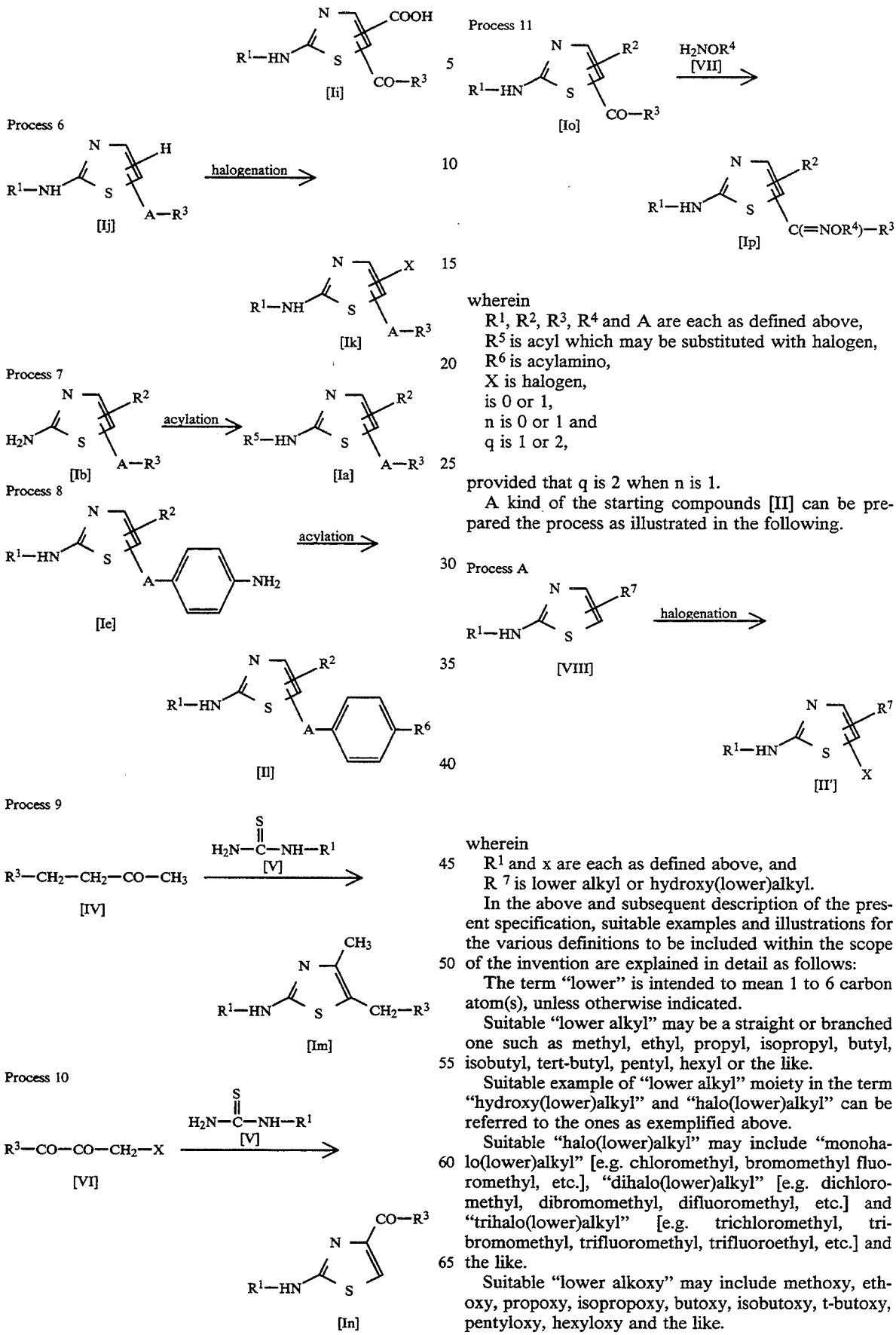

wherein
R¹, R², R³, R⁴ and A are each as defined above,
R⁵ is acyl which may be substituted with halogen,
R⁶ is acylamino,
X is halogen,
is 0 or 1,
n is 0 or 1 and
q is 1 or 2, provided that q is 2 when n is 1.
A kind of the starting compounds [II] can be prepared the process as illustrated in the following.

wherein
R¹ and x are each as defined above, and
R⁷ is lower alkyl or hydroxy(lower)alkyl.

In the above and subsequent description of the present specification, suitable examples and illustrations for the various definitions to be included within the scope of the invention are explained in detail as follows:

The term "lower" is intended to mean 1 to 6 carbon atom(s), unless otherwise indicated.

Suitable "lower alkyl" may be a straight or branched one such as methyl, ethyl, propyl, isopropyl, butyl, isobutyl, tert-butyl, pentyl, hexyl or the like.

Suitable example of "lower alkyl" moiety in the term "hydroxy(lower)alkyl" and "halo(lower)alkyl" can be referred to the ones as exemplified above.

Suitable "halo(lower)alkyl" may include "monohalo(lower)alkyl" [e.g. chloromethyl, bromomethyl fluoromethyl, etc.], "dihalo(lower)alkyl" [e.g. dichloromethyl, dibromomethyl, difluoromethyl, etc.] and "trihalo(lower)alkyl" [e.g. trichloromethyl, tribromomethyl, trifluoromethyl, trifluoroethyl, etc.] and the like.

Suitable "lower alkoxy" may include methoxy, ethoxy, propoxy, isopropoxy, butoxy, isobutoxy, t-butoxy, pentyloxy, hexyloxy and the like.

Suitable "halogen" may include fluorine, chlorine, bromine and iodine.

Suitable examples of "aryl" may include phenyl, tolyl, xylyl, cumenyl, naphthyl, and the like.

Suitable acyl may include an aliphatic acyl, an aromatic acyl and an aliphatic acyl substituted with aromatic group(s).

The aliphatic acyl may include saturated or unsaturated, acyclic or cyclic ones, such as lower alkanoyl (e.g. formyl, acetyl, propionyl, butyryl, sobutyryl, valeryl, isovaleryl, pivaloyl, hexanoyl, etc.), lower alkorycarbonyl (e.g. methoxycarbonyl, ethoxycarbonyl, propoxycarbonyl, butoxycarbonyl, tert-butoxycarbonyl, etc.), lower alkanesulfonyl [e.g. methanesulfonyl, ethanesulfonyl, propanesulfonyl, butanesulfonyl, pentanesulfonyl, hexanesulfonyl, etc.], lower alkenoyl (e.g. acryloyl, methacryloyl, crotonoyl, etc.), carbamoyl and the like.

The aromatic acyl may include aroyl (e.g. benzoyl, toluoyl, xyloyl, etc.) and the like.

The aliphatic acyl substituted with aromatic group(s) may include ar(lower)alkanoyl such as phenyl(lower)alkanoyl (e.g. phenylacetyl, phenylpropionyl, phenylhexanoyl, etc.), ar(lower)alkoxycarbonyl such as phenyl(-lower)alkoxycarbonyl (e.g. benzyloxycarbonyl, phenethyloxycarbonyl, etc.), phenoxy(lower)alkanoyl (e.g. phenoxyacetyl, phenoxypropionyl, etc.), and the like.

Suitable example of "acyl" moiety in the term of "acylamino" can be referred to the ones as exemplified above.

Suitable "N-containing unsaturated heterocyclic group" may be one containing at least one nitrogen atom and may include monocyclic or polycyclic heterocyclic group, and preferable heterocyclic group may be unsaturated 3 to 6 membered heteromonocyclic group containing 1 to 4 nitrogen atoms, for example, pyrrolyl, pyrrolinyl, imidazolyl, pyrazolyl, pyridyl, pyrimidinyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), etc.; unsaturated condensed heterocyclic group containing 1 to 5 nitrogen atoms, for example, indolyl, isoquindolyl, indolizinyl, benzimidazolyl, quinolyl, isoquinolyl, indazolyl, benzotriazolyl, tetrazolopyridazinyl (e.g., zenrazolo[1,5-b]pyridazinyl, etc.), etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.), etc.; unsaturated condensed heterocyclic group containing 1 to 2 oxygen atoms and 1 to 3 nitrogen atoms (e.g., benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.), etc.; unsaturated condensed heterocyclic group containing 1 to 2 sulfur atoms and 1 to 3 nitrogen atoms e.g., henzothiazolyl, benzothiadiazolyl, etc.) and the like. Said "heterocyclic group" may have 1 to 4 substituents such as lower alkyl as exemplified above.

Suitable pharmaceutically acceptable salts of the object compounds [I] are conventional non-toxic salts and include an organic acid salt [e.g. formate, acetate, trifluoroacetate, maleate, tartrate, methanesulfonate, benzenesulfonate, toluenesulfonate, etc.], an inorganic acid salt [e.g. hydrochloride, hydrobromide, sulfate. phosphate, etc.], a salt with an amino acid [e.g. arginine, glutamic acid, ornithine, etc.], a metal salt such as an alkali metal salt [e.g. sodium salt, potassium salt, etc.] and an alkaline earth metal salt [e.g. calcium salt, magnesium salt, etc.], an ammonium salt, an organic base salt [e.g. trimethylamine salt, triethylamine salt, pyridine salt, picoline salt, dicyclohexylamine salt, N,N'-dibenzylethylenediamine salt, etc.], and the like.

In this respect, it is to be noted that the compounds [Ia] to [Ip] are included within the scope of the compound [I], and accordingly the suitable salts of these compounds [Ia] and [Ip] are to be referred to those as exemplified for the object compounds [I] in the above.

The processes for preparing the object compound [I] or salts thereof are explained in detail in the following.

Process 1

The object compound [I] or its salt can be prepared by deacylating a compound [Ia] or its salt.

Suitable method for this deacylation reaction may include conventional one such as hydrolysis and the Like.

Hydrolysis is preferably carried out in the presence of an acid.

Suitable acid may be an inorganic acid [e.g. hydrochloric acid, hydrobromic acid, sulfuric acid, etc.], an organic acid [e.g. formic acid, acetic acid, trifluoroacetic acid, propionic acid, benzenesulfonic acid, p-toluenesulfonic acid, etc.], an acidic ion-exchange resin and the like. In case that the organic acid such as trifluoroacetic acid and p-toluenesulfonic acid is used in this reaction, the reaction is preferably carried out in the presence of cation trapping agents [e.g. anisole, etc.].

The acid suitable for this hydrolysis can be selected according to the kinds of the acyl group to be removed.

The hydrolysis is usually carried out in a conventional solvent which does not adversely influence the reaction such as water, methanol, ethanol, propanol, tert-butyl alcohol, tetrahydrofuran, N,N-dimethylformamide, dioxane or a mixture thereof, and further the above-mentioned acids can also be used as a solvent when they are in liquid.

The reaction temperature of this hydrolysis is not critical, and the reaction is usually carried out under cooling, at ambient temperature or under heating.

In this process, when the starting compound [Ia] or its salt has a acylamino group for $R^3$, the group is also converted to an amino group.

Process 2

The object compound [Ic] or its salt can be prepared by reacting a compound [II] or its salt with a compound [III] or its salt.

Suitable salts of the compound [II] and [III] may be the same as those exemplified as base salts of the object compound [I].

This reaction is usually carried out in a solvent such as methanol, ethanol, propanol, tetrahydrofuran, dioxane, dimethylformamide or any other organic solvent which does not adversely influence the reaction.

In case that a free form of the compound [III] is used in this reaction, the reaction is preferably carried out in the presence of a conventional base, such as alkali metal hydride [e.g. sodium hydride, potassium hydride, etc.], alkaline earth metal hydride [e.g. calcium hydride, magnesium hydride, etc.], alkali metal hydroxide [e.g. sodium hydroxide, potassium hydroxide, etc.], alkali metal carbonate [e.g. sodium carbonate, potassium carbonate, etc.], alkali metal bicarbonate [e.g. sodium bicarbonate, potassium bicarbonate, etc.], alkali metal fluoride [e.g. potassium fluoride, cesium fluoride, etc.], alkali metal alkoxide [e.g. sodium methoxide, sodium ethoxide, potassium tert-butoxide, etc.], trialkylamine [e.g. trimethylamine, triethylamine, etc.], picoline, 1,5-diazabicyclo[4,3,0]non-5-ene, 1,4-diazabicyclo[2,2,2-]octane, 1,5-diazabicyclo[5,4,0]undecene-5 or the like.

The reaction temperature is not critical, and the reaction is usually carried out at ambient temperature or under cooling, warming or heating.

Process 3

The object compound [Ie] or its salt can be prepared by reducing a compound [Id] or its salt.

The reduction can be carried out in a conventional manner, namely, chemical reduction or catalytic reduction.

Suitable reducing agents to be used in chemical reduction are a combination of metal (e.g. stannum, zinc, iron, etc.) and ammonium chloride or an base (e.g. ammonia, sodium hydroxide, etc.), a combination of metal (e.g. tin, zinc, iron, etc.) or metallic compound (e.g. chromium chloride, stannous chloride, chromium acetate. etc.) and an organic or inorganic acid (e.g. formic acid, acetic acid, propionic acid, trifluoroacetic acid, p-toluenesulfonic acid, hydrochloric acid, hydrobromic acid, etc.), alkali metal borohydride (e.g. lithium borohydride, sodium borohydride, potassium borohydride, etc.) alkali metal cyanoborohydride (e.g. sodium cyanoborohydride, etc.) or alkali metal ammonium hydride (e.g. lithium aluminum hydride, etc.) or the like.

Suitable catalysts to be used in catalytic reduction are conventional ones such as platinum catalyst (e.g. platinum plate, spongy platinum, platinum black, colloidal platinum, platinum oxide, platinum wire, etc.), palladium catalyst (e.g. palladium on carbon, colloidal palladium, palladium on barium sulfate, palladium on barium carbonate, etc.), nickel catalyst (e.g. reduced nickel, nickel oxide, Raney nickel, etc.), cobalt catalyst (e.g. reduced cobalt, Raney cobalt, etc.), iron catalyst (e.g. reduced iron, Raney iron, etc.), copper catalyst (e.g. reduced copper, Raney copper, Ullman copper, etc.) or the like.

The reduction of this process is usually carried out in a solvent such as water, alcohol (e.g. methanol, ethanol, propanol, etc.), acetic acid, dioxane, tetrahydrofuran, N,N-dimethylformamide, dimethyl sulfoxide, or any other organic solvent which does adversely influence the reaction, or a mixture thereof. In case above-mentioned reducing agent is liquid, it can be also used as a solvent.

The reaction is preferably carried out under cooling to warming or heating.

Process 4

A compound [Ig] or its salt can be prepared by subjecting a compound [If] or its salt to oxidation.

Oxidation in this process is carried out in a conventional manner with a conventional oxidizing agent which can oxidize a —S— group into —SO— or —SO$_2$—group, or —SO— group into —SO$_2$— group.

Suitable example of such oxidizing agent are inorganic peracid or its salt (e.g. periodic acid, persulfuric acid, etc.) or the sodium or potassium salt thereof, an organic peracid or its salt (e.g. perbenzoic acid, 3-chloroperbenzoic acid, performic acid, peracetic acid, chloroperacetic acid, trifluoroperacetic acid, etc. or the sodium or potassium salt thereof, etc.), ozone, hydrogen peroxide, urea-hydrogen peroxide and the like.

The present reaction is preferably conducted in the presence of a compound comprising a Group Vb or VIb metal in the Periodic Table, for example, tungstic acid, molybdic acid, vanadic acid, etc. or their salt with an alkali metal (e.g. sodium, potassium, etc.), an alkaline earth metal (e.g. calcium, magnesium, etc.) or ammonium, etc., or vanadium pentoxide.

The present oxidation is usually conducted in a solvent such as water, acetic acid, ethyl acetate, chloroform, dichloromethane, tetrahydrofuran, dioxane, N,N-dimethylformamide or any other solvent which does not give bad influence to the present reaction.

There is not particular limitation to the reaction temperature, and the present reaction is usually conducted at ambient temperature or under cooling.

Process 5

The object compound [Ii] or its salt can be prepared by subjecting a compound [Ih] or its salt to oxidation.

Suitable oxidizing agent may include hypochlorite compound (e.g. tert-butyl hypochlorite, etc.), permanganate (e.g. potassium permanganate, etc.), or any other conventional oxidizing agent.

This reaction is usually carried out in a solvent such as water, acetic acid, diethyl ether, dioxane, dichloromethane, chloroform, N,N-dimethylformamide, dimethyl sulfoxide, or any other organic solvent which does not adversely influence the reaction, or a mixture thereof. In case the above-mentioned acid is liquid, it can be also used as a solvent.

The reaction can be carried out under cooling to warming or heating.

Process 6

The object compound [Ik] or its salt can be prepared by halogenating a compound [Ij] or its salt.

Suitable halogenating agent of this reaction may include conventional ones for example, halogen [e.g. chlorine, bromine, iodine, etc.], sulfuryl halide [e.g. sulfuryl chloride, sulfuryl bromide, etc.], N-halosuccinimide [e.g. N-chlorosuccinimide, N-bromosuccinimide, etc.], pyridinium hydrohalide perhalide [e.g. pyridinium hydrobromide perbromide, pyridinium hydrochloride perchloride, etc.], quarternary ammonium perhalide [e.g. phenyltrimethylammonium perbromide, etc.], ω-trihaloacetophenone [e.g. ω-tribromoacetophenone, etc.], cupric or potassium bromide, selenium oxychloride, or the like. These halogenating agents may be selected according to the kind of the starting compound [Ij] to be used.

This reaction is usually carried out in a conventional solvent such as chloroform, methylene chloride, carbon tetrachloride, acetic acid, a mixture of hydrogen halide [e.g. hydrogen bromide, hydrogen chloride, etc.] and acetic acid, water, dimethylformamide or the like.

The reaction temperature is not critical, and the reaction is usually carried out under cooling, at ambient temperature or under warming or heating.

Process 7

The object compound [Ia] or its salt can be prepared by acylating a compound [Ib] or its reactive derivatives at the amino group or a salt thereof.

Suitable reactive derivatives at the amino group of the compound [Ib] include conventional ones used in amidation for example, Schiff's base type imino or its tautomeric enamine type isomer formed by reaction of a compound [Ib] with a carbonyl compound, a silyl derivative formed by reaction of a compound [Ib] with a silyl compound such as trimethylsilylacetamide, bis(trimethylsilyl)acetamide or the like, a derivative formed by reaction of a compound [Ib] with phosphorus trichloride or phosgene, and the like.

Suitable acylating agent to be used in this reaction includes an organic acid such as alkanoic acid [e.g. formic acid, acetic acid, propionic acid, etc.], arenecarboxylic acid (e.g. benzoic acid, toluenecarboxylic acid, etc.) which may have halogen, lower alkanesulfonic acid [e.g. methanesulfonic acid, etc.], arylisocyanate [e.g. phenylisocyanate, etc.] which may have halogen and their reactive derivative.

The suitable reactive derivative may be a conventional one such as an acid halide [e.g. acid chloride, acid bromide, etc.], an acid azide, an acid anhydride, an activated amide, an activated ester and the like. When free acid is used as an acylating agent, the acylation reaction may preferably be conducted in the presence of a conventional condensing agent such as N,N'-dicyclohexylcarbodiimide or the like.

This reaction is usually carried out in a solvent which does not adversely influence the reaction such as water, tetrahydrofuran, chloroform, dioxane, pyridine, methylene chloride, N,N-dimethylformamide or the like.

The reaction temperature is not critical and the reaction can be carried out at any temperature under cooling to heating.

Process 8

The object compound [Il] or its salt can be prepared by acylating a compound [Ie] or its reactive derivatives at the amino group or a salt thereof.

Suitable reactive derivatives at the amino group are to be referred to those as exemplified in Process 7.

This reaction may be carried out in substantially the same manner as Process 7, and therefore the reaction mode and reaction conditions [e.g. acylating agent, solvent, reaction temperature, etc.] of this reaction are to be referred to those as explained in Process 7.

Process 9

The object compound [Im] or its salt can be prepared by reacting a compound [IV] or its salt with a compound [V] or its salt.

Suitable salts of the compounds [IV] and [V] may be the same as those exemplified for the compound [I].

Suitable examples of the compound IV] may be thiocarbamoyl derivatives such as thiourea, N-acylthiourea [e.g. N-formylthiourea, N-acetylthiourea, N-propionylthiourea, N-benzoylthiourea which may be substituted with halogen, etc.] or the like.

This reaction is usually carried out in a conventional solvent such as water, methanol, ethanol. isopropyl alcohol, tetrahydrofuran, dioxane, chloroform, methylene chloride, dimethylacetamide, dimethylformamide or any other organic solvent which does not adversely influence the reaction. Among these solvents, hydrophilic solvents may be used in a mixture with water.

The reaction temperature is not critical, and the reaction is usually carried out at ambient temperature or under warming or heating.

Process 10

The object compound [In] or its salt can be prepared by reacting a compound [VI] or its salt with a compound [V] or its salt.

Suitable salts of the compound [VII may be the same as those exemplified for the object compound [I].

This reaction may be carried out in substantially the same manner as Process 9, and therefore the reaction mode and reaction conditions [e.g. solvent, reaction temperature, etc.] of this reaction are to be referred to those as explained in Process 9.

Process 11

The object compound [Ip] or its salt can be prepared by reacting a compound [Io] or its salt with a hydroxylamine derivative [VII] or its salt.

A suitable salt of a hydroxylamine derivative [VII] may be a hydrohalide (e.g. hydrochloride, etc.).

This reaction is usually carried out in a conventional solvent such as water, alcohol (e.g. methanol, ethanol, propanol, etc.), tetrahydrofuran, dioxane, ethyl acetate, N,N-dimethylformamide, dimethyl sulfoxide or any other organic solvent which does not adversely influence the reaction. In case the compound [VII] is liquid, it can be also used as a solvent.

The reaction temperature is not critical, and the reaction can be carried out under cooling to warming or heating.

The process for preparing the starting compound [II] or its salt is explained in detail in the following.

Process A

The compound [II'] or its salt can be prepared by halogenating a compound [VIII] or its salt.

Suitable salts of the compounds [II'] and [VII] may be the same as those exemplified for the object compound This reaction may be carried out in substantially the same manner as Process 6, and therefore the reaction mode and reaction conditions [e.g. halogenating agent, solvent, reaction temperature, etc.] of this reaction are to be referred to those as explained in Process 6.

The object compounds and pharmaceutically acceptable salts thereof are novel and exhibit pharmacological activities and are useful for the treatment and prophylaxis of rheumatism (e.g. rheumarthritis, etc.], nephritis, thrombocytopenia [e.g. idiopathic thrombocytopenic purpura, secondary thrombocytopenic purpura, thrombocytopenia due to a side effect of an antitumor agent (e.g. mitomycin C, etc.) etc.], tumor, side effect of an antitumor agent (e.g. decrease of body weight, etc.) and the like.

In order to show the utility of the object compounds [I], antirheumatic, anti-nephritic and platelet number-increasing activities and alleviating activity for side effect of antitumor agent of the object compounds [I] are explained in the following.

Antirheumatic Activity

Test 1

Effect on Collagen Induced Arthritis in Mice

Method:

Ten male DBA/1 mice were used per group. Type II bovine collagen was dissolved in 0.1M acetic acid and emulsified in complete Freund's adjuvant (CFA). Mice were primed with 125 $\mu$g of Type II collagen in CFA intradermally at the base of the tail. Mice were challenged after 21 day with the same procedure. From the day of challenge, drug was administered orally once a day for 3 weeks and mice were inspected weekly for visual signs of arthritis. To evaluate the effect of drugs, an arthritic index was used. Arthritic index was obtained by scoring each limb 0-3 severity, representing join swelling and erythema (Grade 1), visible joint disorder (Grade 2) and detectable joint ankylosis (Grade 3), and by summing up scores of four limbs.

Results:

| Compounds | Dose level (mg/kg) | Inhibition (%) |
|---|---|---|
| a compound of | | |
| Example 18 | 100 | 50 |
| Example 23 | 100 | 51 |
| Example 27 | 100 | 46 |
| Example 29 | 100 | 57 |
| Example 30 | 100 | 35 |
| Example 33 | 100 | 44 |
| Example 37 | 100 | 50 |
| Example 38 | 100 | 31 |
| Example 40 | 100 | 44 |

Anti-Nephritic Activity

Test 2

Effect on Chloric GVH Disease (Nephritis)

Method:

Six weeks old female (57BL/6×DBA/2)$F_1$ and DBA/2 mice were used. Graft-versus-host (GVH) disease was induced in (57BL/6×DBA/2)$F_1$ mice with two injections of DBA/2 spleen cells given 5 days apart. Each injection contained $5\times10^7$ cells. From 3 days after second cell injection, drug was administered orally once a day for 8 weeks. To assess the renal disease, at 8 weeks after last cell injection, proteinuria were measured. The concentration of serum albumin in the urine was determined by the single radial immunodiffusion method using rabbit anti-mouse serum albumin antiserum. Ten mice were used per group. Antinephritic activity of the compound was expressed the inhibition of albumin in urine.

Results:

| Compounds | Dose level (mg/kg) | Inhibition of albumin in urine (%) |
|---|---|---|
| a compound of | | |
| Example 7 | 100 | 52 |
| Example 18 | 100 | 98 |
| Example 23 | 100 | 96 |
| Example 29 | 100 | 90 |
| Example 30 | 100 | 98 |
| Example 33 | 100 | 70 |
| Example 35 | 100 | 74 |
| Example 37 | 100 | 100 |
| Example 38 | 100 | 78 |

Platelet Number-Increasing Activity

Test 3

Increasing Effect on the Platelet Number Decreased by Mitomycin C

Method:

A test compound was given orally once a day for 5 days to male ddY mice aged 6 or 7 weeks. The animals were used in groups of 10. Mitomycin C (hereinafter referred to as MMC) at a dose of 3.2 mg/kg was given intravenously to mice on day 0, 2 and 4 after the initial dosing with the test compound. The number of platelets were counted 5 days after the final dosing with the test compound, in which mice were bled from the orbital plexus and the platelets were counted with an automatic blood analyzer. The number of platelets of each group was calculated on the basis of the number of platelets (%) obtained from the non-test compound group.

Results:

| Compounds | Dose level (mg/kg) | Number of platelets (%) |
|---|---|---|
| a compound of | | |
| Example 14 | 32 | 164 |
| Example 15 | 32 | 150 |
| Example 30 | 32 | 184 |
| Example 31 | 32 | 154 |
| Example 33 | 32 | 210 |
| Example 40 | 32 | 165 |
| Example 68 | 32 | 135 |

Alleviating Activity for Side Effect of Antitumor Agent

Test 4

Restoring Effect on the Body Weight Decreased by MMC

Method:

A test compound was given orally once a day for 5 days to male ddY mice aged 6 or 7 weeks. The animals were used in groups of 10. MMC at a dose of 3.2 mg/kg was given intravenously to mice on day 0, 2 and 4 after the initial dosing with the test compound. The body weight of mice were measured on day 0 and day 8.

The body weight of non-test compound group which was only administered MMC as above was measured on day 0 and day 8 as a control.

Results:

| | Dose of test compound (mg/kg) | Body weight (g) | |
|---|---|---|---|
| | | day 0 | day 8 |
| MMC & a compound of Example 30 | 100 | 32.7 | 31.1 |
| MMC & a compound of Example 31 | 100 | 32.6 | 31.1 |
| MMC & a compound of Example 68 | 100 | 32.6 | 30.2 |
| MMC (no test compound) | — | 32.6 | 28.6 |

(mean of 10 mice)

For therapeutic administration, the object compounds [I] and pharmaceutically acceptable salts thereof are used in the form of conventional pharmaceutical composition such as pewdews, fine granules, granules, tablets, dragee, miorocapsules, capsules, suppository, solution, suspension, emulsion, syrups and the like. If desired, diluents or disintegrators (e.g. sucrose, lactose, starch, crystalline cellulose, low-substituted hydroxypropyl cellulose, synthetic aluminum silicate, etc.), binding agents (e.g. cellulose, methylcellulose, hydroxypropylcellulose, hydroxypropylmethylcellulose, polypropylpyrrolidone, polyvinylpyrrolidone, gelatin, gum arabic, polyethyleneglycol, etc.), coloring agents, sweeting agents, lubricant (e.g. magnesium stearate, etc.) or the like, may be dispensed with said composition.

The dosage of said composition according to this invention depends on the patient's age, body weight, condition, etc., and it is generally administered by the oral route at the daily dose level of 1 mg to 1 g as the object compound [I] or a salt thereof, preferably 10 mg to 100 mg on the same basis, at the interval of 1 to 3 times a day. Typical unit doses may be 5 mg, 10 mg, 20 mg, 50 mg, 100 mg and the like, although these are only examples and not limitative, of course.

The following Preparations and Examples are given for the purpose of illustrating the present invention in more detail.

Preparation 1

A mixture of 2-acetylamino-4-hydroxymethylthiazole (7.0 g) and N-chlorosuccinimide (6.5 g) in acetic acid ml) was heated at 40° C. for 3.5 hours with stirring. The reaction mixture was concentrated under reduced pressure and the residue was added the aqueous sodium bicarbonate. The mixture was extracted with a mixture of ethyl acetate and tetrahydrofuran (1:1), washed with water and dried over magnesium sulfate. The solvent was concentrated under reduced pressure and the residue was triturated with isopropyl ether. The precipitates were collected by filtration, washed with isopropyl ether and dried in vacuo to give 2-acetylamino-5-chloro-4-hydroxymethylthiazole (73 g, yield: 78.5%).

mp: 145°–146° C. IR (Nujol): 3150, 1690, 1550, 1285 cm$^{-1}$ NMR (DMSO-d$_6$, 60 MHZ, ppm): 2.17 (3H, s), 4.17 (2H, d, J=5 Hz), 5.17 (1H, t, J=5 Hz) Mass: M$^{+2}$ 208, M$^{+1}$ 207, M 206, m/e 164, 147, 135

Preparation 2

A mixture of 2-amino-4-methylthiazole hydrochloride (1.5 g) and N-chlorosuccinimide (1.6 g) in acetic acid (15 ml) was heated 40° C. for 5.5 hours with stirring. The reaction mixture was poured into ice water and the solution was adjusted to pH 8.5 using sodium bicarbonate. The mixture was extracted with a mixture of tetrahydrofuran and ethyl acetate (1:1), washed with aqueous saturated sodium chloride and dried over magnesium sulfate. The solvent was concentrated under reduced pressure to give 2-amino-5-chloro-4-methylthiazole (1.4 g, yield: 94.6%, oil).

NMR (DMSO-d$_6$, 200 MHZ, ppm): 2.09 (3H, s), 7.00 (2H, br s) Mass: M$^{+2}$ 150, M$^{+1}$ 149, M 148, m/e 133,113, 99

Preparation 3

To a solution of 2-amino-4-methylthiazole hydrochloride (3.0 g) in acetic acid (20 ml) was added once N-bromosuccinimide (4.0 g) at room temperature with stirring. The mixture was stirred at room temperature for 1.5 hours and the reaction mixture was poured into isopropyl ether under ice cooling. The precipitates were collected by filtration, washed with ethyl ether and dried in vacuo to give 2-amino-5-bromo-4-methylthiazole hydrochloride (4.1 g, yield: 89.1%).

mp: 175°–178° C. (dec.) IR (Nujol): 3200, 2500–2700, 1635 cm$^{-1}$ NMR (DMSO-d$_6$, 200 MHZ, ppm): 2.14 (3H, s), 8.90 (3H, br s) Mass: M$^{+3}$ 196, M$^{+2}$ 195, M$^{+1}$ 194, M 193, m/e 192, 191, 149, 123, 113

EXAMPLE 1

A solution of 1-acetyl-2-(4-nitrophenyl)ethane (9.6 g) and pyridinium bromide perbromide (18 g) in acetic acid and 35% hydrogen bromide in acetic acid (21 ml) was stirred at room temperature for 5 hours. The reaction mixture was washed with isopropyl ether and decanted. To the residue was added the thiourea (6 g), sodium acetate (8 g) and ethanol (150 ml). The mixture was heated at 50° C. for 2 hours with stirring. The reaction mixture was concentrated in vacuo and to the residue was added water and then the mixture was adjusted to pH 8. The solution was extracted with ethyl acetate and washed with 10% aqueous hydrochloric acid and dried over magnesium sulfate. The solvent was concentrated in vacuo and the residue was subjected to column chromatography on silica gel (silica gel 60, 70–230 mesh; Merck: 300 g) and eluted with a mixture of chloroform and methanol (10:1). The fractions containing the objective compound were combined and concentrated under reduced pressure to give 2-amino-4-methyl-5-(4-nitrobenzyl)thiazole (2.0 g, yield: 16.2%).

IR (Nujol): 3200, 3250, 3350, 1630, 1605, 1515, 1350 cm$^{-1}$ NMR (DMSO$_6$, 90 MHZ, ppm): 2.20 (3H, s), 4.10 (2H, s), 7.50 (2H, d, J=9 Hz), 8.16 (2H, d, j=9 Hz), 8.85 (2H, s) Mass: M$^{+1}$ 250, M 249, m/e 234, 204, 190, 127

EXAMPLE 2

To a solution of potassium permanganate (4 g) in water (400 ml) was portionwise added the 2-amino-4-methyl-5-(4-nitrobenzyl)thiazole (2.3 g) at 80°–90° C. with stirring. The mixture was refluxed for 2 hours with stirring. The reaction mixture was filtered and then the filtrate was adjusted to pH 2.0 using diluted aqueous hydrochloric acid under ice cooling. The precipitates were collected by filtration, washed with water and dried in vacuo to give 2-amino-5-(4-nitrobenzoyl)-4-thiazole carboxylic acid (1.50 g, yield: 75.0%).

IR (Nujol): 3500, 2650, 2550, 1710, 1690, 1605, 1525, 1350 cm$^{-1}$ NMR (DMSO-d$_6$, 60 MHZ, ppm): 7.70 (2H, s), 8.25 (2H, d, J=10 Hz), 8.43 (2H, d, J=10 Hz) Mass: M 293, m/e 192, 167

EXAMPLE 3

A mixture of 2-amino-5-(4-nitrobenzoyl)-4-thiazolecarboxylic acid (2.6 g) and 10% palladium on carbon (1 g, 50% wet) in a mixture of methanol (50 ml) and tetrahydrofuran (50 ml) was hydrogenated under atmospheric pressure for 2 hours. The reaction mixture was filtered and then the filtrate was concentrated under reduced pressure. The residue was triturated with ether and the precipitates were collected by filtration, washed with ether and dried in vacuo to give 2-amino-5-(4-aminobenzoyl)-4-thiazolecarboxylic acid (2.10 g, yield: 90.0%).

mp: 290°–295° C. (dec.) IR (Nujol): 3470, 3370, 2700–2500, 1690–1660, 1600 cm$^{-1}$ NMR (DMSO-d$_6$, 60 MHZ, ppm): 5.73 (2H, br s), 6.80 (2H, d, J=10 Hz), 6.80 (2H, br s), 7.70 (2H, d, J=10 Hz) Mass: m/e 220, 205, 151, 137, 120

EXAMPLE 4

A mixture of chloromethyl-(4-nitrophenyl)diketone (2 g), thiourea (1.5 g) and sodium acetate (1.6 g) in ethanol (20 ml) was heated at 50° C. for 4 hours with stirring. The mixture was concentrated in vacuo and the residue was triturated with water. The precipitates were collected by filtration, washed with water and dried in vacuo to give solid. The solid was subjected to column chromatography on silica gel (silica gel 60, 70–230 mesh; Merck: 100 g) and eluted with a mixture of chloroform and methanol (10:1). The fractions containing the objective compound were combined and concentrated under reduced pressure give 2-amino-4-(4-nitrobenzoyl)thiazole (0.71 g, yield: 32.4%).

mp: 194°–198° C. (dec.) IR (Nujol): 3300–3450, 1660, 1600, 1520, 1350 cm$^{-1}$ NMR (DMSO-$d_6$, 90 MHZ, ppm): 7.30 (2H, s), 7.60 s), 8.15 (2H, d, J=9 Hz), 8.30 (2H, d, J=9 Hz) Mass: M$^{+1}$ 250, M 249, m/e 219, 205,150, 99

EXAMPLE 5

A mixture of 2-amino-4-(4-nitrobenzoyl)thiazole g) and 10% palladium on carbon (1 g, 50% wet) in a mixture of tetrahydrofuran (50 ml), methanol (50 ml) and acetic acid (5 ml) was hydrogenated under atmospheric pressure for 7 hours. The reaction mixture was filtered and then, the filtrate was concentrated under reduced pressure. The residue was dissolved in water and adjusted to pH using aqueous sodium bicarbonate. The precipitates were collected by filtration, washed with water and dried in vacuo to give 2-amino-4(4-aminobenzoyl)thiazole (0.54 g, yield: 87.7%).

mp: 180°–184° C. (dec.) IR (Nujol): 3150, 3350, 3450, 1620, 1595 cm$^{-1}$ NMR (DMSO-$d_6$, 90 MHZ, ppm): 6.00 (2H, s), 6.55 (2H), d, J=9 Hz), 7.10 (2H, s), 7.25 (1H, s), 7.93 (2H, d, J=9 Hz) Mass: M$^{+1}$ 220, M 219, m/e 209, 160, 120

EXAMPLE 6

A mixture of 2-amino-4-(4-aminobenzoyl)thiazole (6 g) and methoxyamine hydrochloride (13 g) in methanol (800 ml) was stirred at room temperature for 16 hours. The reaction mixture was concentrated under reduced pressure and then to the residue was added water. The solution was adjusted to pH 8.5 using 10% aqueous sodium bicarbonate under ice-cooling. The precipitates were collected by filtration, washed with water and recrystallized from ethanol to give 2-amino-4-[(4-aminophenyl)methoxylminomethyl]thiazole (4.9 g, yield: 72.1%).

mp: 181°–183° C. IR (Nujol): 3350, 3100, 1605, 1510, 1380 cm$^{-1}$ NMR (DMSO-$d_6$, 60 MHZ, ppm): 3.73 (3H, s), 5.29 (2H, s), 6.46 (2H, d, J=9 Hz), 6.95 (1H, s), 7.00 (2H, d, J=9 Hz) Mass: M$^{+1}$ 249, M 248, m/e 217, 203

EXAMPLE 7

To a mixture of 2-amino-5-(4-nitrophenylsulfonyl)-thiazole (4.0 g) and ammonium chloride in a mixture of ethanol (80 ml), tetrahydrofuran (40 ml) and water (30 ml) was portionwise added the iron powder (4 g) at 80° C. with stirring. The mixture was refluxed for 1.5 hours with stirring. The reaction mixture was filtered by suction and the filtrate was concentrated under reduced pressure. The residue was triturated with water and the precipitates were collected by filtration, washed with water and dried in vacuo no give 2-amino-5-(4-aminophenylsulfonyl)thiazole (3.10 g, yield: 86.6%).

mp: 218°–219° C. IR (Nujol): 3400, 3300, 1620, 1595, 1535, 1380 cm$^{-1}$ NMR (DMSO-$d_6$, 90 MHZ, ppm): 6.07 (2H, s), 6.57 (2H, d, j=9 Hz), 7.43 (2H, d, J=9 Hz), 7.40 (1H, s), 7.77 (2H, s) Mass: M$^{+1}$ 256, M 255, m/e 191, 140

EXAMPLE 8

A mixture of 2-acetylamino-4-chloromethylthiazole (1.9 g), 4-nitrothiophenol (1.6 g) and potassium carbonate (2.0 g) in a N,N-dimethylformamide (50 ml) was heated at 100° C. for 3 hours with stirring. The reaction mixture was concentrated under reduced pressure and the residue was triturated with water. The precipitates were collected by filtration, washed with water and dried in vacuo to give 2-acetylamino-4-(4-nitrophenyl-thiomethyl)thiazole (2.95 g, yield: 95.5%).

mp: 165°–166° C. IR (Nujol): 3150, 1655, 1595, 1545, 1500, 1335, 1290 cm$^{-1}$ NMR (DMSO-$d_6$, 60 MHZ, ppm): 2.17 (3H, s), 4.67 (2H, s), 7.15 (1H, s), 7.60 (2H, d, J=8 Hz), 8.17 (2H, d, J=8 Hz) Mass: M$^{+1}$ 310, M 309, m/e 267, 246, 155, 124, 113

EXAMPLE 9

To a mixture of 2-acetylamino-4-(4-nitrophenylthiomethyl)thiazole (11 g) and ammonium chloride (2 g) in a mixture of tetrahydrofuran (200 ml), ethanol (200 ml) and water (100 ml) was added portionwise the iron powder (17 g) at 80° C. with stirring. The mixture was refluxed for 3 hours with stirring. The reaction mixture was filtered by suction and the filtrate was concentrated under reduced pressure and then the residue was triturated with water. The precipitates were collected by filtration, washed with water and dried in vacuo to give 2-acetylamino-4-(4-aminophenylthiomethyl)thiazole (9.3 g, yield: 93.6%).

IR (Nujol): 3400, 3250, 3150, 1690, 1545, 1370, 1220 cm$^{-1}$ NMR (DMSO-$d_6$, 90 MHZ, ppm): 2.10 (3H, s), 3.90 (2H, s), 5.20 (2H, s), 6.50 (2H, d, J=8 Hz), 6.70 (1H, s), 7.05 (2H, d, J=8 Hz), 12.10 (1H, s) Mass: M$^{+1}$ 280, M 279, m/e 236, 220, 216, 205

EXAMPLE 10

To a solution of 2-acetylamino-4-(4-aminophenylthiomethyl)thiazole (9.0 g) in ethyl acetate (300 ml) was added portionwise the 3-chloroperbenzoic acid (17 g) at 5° C. with stirring. The mixture was stirred at room temperature for 16 hours. The reaction mixture was washed with aqueous sodium bicarbonate and dried over magnesium sulfate. The solvent was concentrated under reduced pressure to give solid. The solid was subjected to column chromatography on silica gel (silica gel 60, 70–230 mesh; Merck: 300 g) and eluted with a mixture of chloroform and methanol (10:1). The fractions containing the objective compound were combined and concentrated under reduced pressure to give 2-acetylamino-4-(4-aminophenylsulfonylmethyl)-thiazole (4.85 g, yield: 48.3%).

mp: 135°–137° C. IR (Nujol): 3450, 3350, 3200, 1680, 1635, 1595 1550, 1300 cm$^{-1}$ NMR (DMSO-$d_6$, 60 MHZ, ppm): 2.17 (3H, s), 4.50 (2H, s), 6.17 (2H, s), 6.63 (2H, d, J=8 Hz), 6.90 (1H), 7.35 (2H, d, J=8 Hz)

EXAMPLE 11

A solution of 2-acetylamino-4-(4-aminophenylsulfonylmethyl) thiazole (4.8 g) in a mixture of acetic acid (35 ml) and 6N-aqueous hydrochloric acid (10 ml) was refluxed for 2.5 hours with stirring. The reaction mixture was poured into ice-water and then the solution was adjusted to pH 8.0 using 10% aqueous sodium bicarbonate with stirring. The precipitates were collected by filtration, washed with water and dried in vacuo to give 2-amino-4-(4-aminophenylsulfonylmethyl)thiazole (2.50 g, yield: 60.2%).

mp: 203°–206° C. (dec.) IR (Nujol): 3450, 3350, 1630, 1595, 1530 1380 cm$^{-1}$ NMR (DMSO-d$_6$, 60 MHZ, ppm): 4.20 (2H s) 6.03 (2H, s), 6.27 (1H, s), 6.57 (2H, d, J=8 Hz), 6.85 (2H, s), 7.33 (2H, d, J=8 Hz) Mass: M 269, m/e 205, 162, 140, 113

EXAMPLE 12

A mixture of 4-nitrothiophenol (9.3 g), 2-amino-4-chloromethylthiazole hydrochloride (11 g) and potassium carbonate (20 g) in N,N-dimethylformamide (200 ml) was heated at 85°–90° C. for 5 hours with stirring. The reaction mixture was concentrated under reduced pressure and the residue was triturated with water. The precipitates were collected by filtration, washed with water and dried in vacuo to give 2-amino-4-(4-nitrophenylthiomethyl)thiazole (15.80 g, yield: 98.6%).

IR (Nujol): 3400, 3100, 1630, 1530, 1340 cm$^{-1}$ NMR (DMSO-d$_6$, 60 MHZ, ppm): 4.23 (2H, s), 6.60 (1H, s), 7.03 (2H, s), 7.63 (2H, d, J=9 Hz), 8.20 (2H, d, J=9 Hz)

EXAMPLE 13

To a mixture of 2-amino-4-(4-nitrophenylthiomethyl)thiazole (15 g) and ammonium chloride (2 g) in a mixture of tetrahydrofuran (100 ml), ethanol (150 ml) and water was added portionwise added the iron powder (15 g) at 80° C. with stirring. The mixture was refluxed for 2 hours with stirring. The reaction mixture was filtered by suction and the filtrate was concentrated under reduced pressure. The residue was extracted with a mixture of tetrahydrofuran and ethyl acetate (1:1), washed with saturated aqueous sodium chloride and dried over magnesium sulfate. The solvent was evaporated in vacuo and the residue was triturated with chloroform. The precipitates were collected by filtration, washed with ether and dried in vacuo to give 2-amino-4-(4-aminophenylthiomethyl)thiazole (10.50 g, yield: 73.0%).

mp: 130°–132° C. IR (Nujol): 3425, 3350, 1630, 1605, 1595, 1535, 1495, 1440, 1380, 1340, 1280 cm$^{-1}$ NMR (DMSO-d$_6$, 90 MHZ, ppm): 3.70 (2H, s), 5.15 (2H, s), 6.10 (1H, s), 6.45 (2H, d, J=9 Hz), 6.83 (2H, s), 7.00 (2H, d, J=9 Hz) Mass: M$^{+1}$238, M 237, m/e 204, 124, 113

EXAMPLE 14

A solution of 3-chloroperbenzoic acid (4.9 g) in dichloromethane (100 ml) was dropwise added to a solution of 2-amino-4-(4-aminophenylthiomethyl)thiazole (5.1 g) in a mixture of dichloromethane (200 ml) and N,N-dimethylformamide (10 ml) at 5° C. with stirring. The mixture was stirred at 5° C. for 1.5 hours with stirring. The precipitates were collected by filtration, washed with ethyl acetate and dried in vacuo to give solid. The solid was recrystallized from ethanol to give 2-amino-4-(4-aminophenylsulfinylmethyl)thiazole (4.70 g, yield: 86.3%).

IR (Nujol): 3350–3100, 1620, 1600, 1500, 1380, 1300 cm$^{-1}$ NMR (DMSO-d$_6$, 60 MHZ, ppm): 3.87 (2H, s), 6.27 (2H, s), 6.67 (2H, d, J=9 Hz), 7.00 (2H, 7.30 (2H, d, j=9 Hz), 7.67 (1H, s) Mass: M$^{+1}$ 254, M 253, m/e 237, 205, 156, 139

EXAMPLE 15

To a solution of 2-amino-4-(4aminophenylsulfinylmethyl)thiazole (2.8 g) in N,N-dimethylformamide (30 ml) was added portionwise the 3-chloroperbenzoic acid (2.6 g) at 5° C. with stirring. The mixture was stirred at room temperature for 2 hours and then the solution was poured into ice-water. The precipitates were collected by filtration, washed with aqueous sodium bicarbonate, washed with water and dried in vacuo to give 2-amino-4-(4-aminophenylsulfonylmethyl)thiazole (2.85 g, yield 95.6%).

mp: 204°–208° C. (dec.) IR (Nujol): 3375, 3275, 3150, 1615, 1595, 1295, 1140 cm$^{-1}$ NMR (DMSO-d$_6$, 60 MHZ, ppm): 4.30 (2H, s), 6.10 (2H, s), 6.30 (1H, s), 6.67 (2H, d, J=8 Hz), 6.95 (2H, s), 7.43 (2H, d, J=8 Hz) Mass: M 269, m/e 220, 205

EXAMPLE 16

A mixture of 2-acetylamino-5-chlorothiazole (5 g), 4-nitrothiophenol (4.83 g) and potassium carbonate (7.8 g) in N,N-dimethylformamide (100 ml) was heated at 120° C. for hours with stirring. The reaction mixture was poured into ice-water. The precipitates were collected by filtration, washed with water and dried in vacuo to give solid. The solid was subjected to column chromatography on silica gel (silica gel 60, 70–230 mesh; Merck: 200 g) and eluted with a mixture of n-hexane and ethyl acetate (3:1). The fractions containing the objective compound were combined and concentrated under reduced pressure give 2-acetylamino-5-(4-nitrophenylthio)thiazole (3.74 g, yield: 50.2%)

mp: 250°–255° C. (dec.) IR (Nujol): 3150, 1695, 1595, 1550, 1505, 1340, 1300, 1230 cm$^{-1}$ NMR (DMSO-d$_6$, 60 MHZ, ppm): 2.23 (3H, s), 7.40 (2H, d, J=8 Hz), 7.90 (1H, s), 8.23 (2H, d, j=8 Hz), 12.43 (1H, br s) Mass: M$^{+1}$ 296, M 295, m/e 265, 253, 223, 181, 166

EXAMPLE 17

To a mixture of 2-acetylamino-5-(4-nitrophenylthio)thiazole (2.8 g) and ammonium chloride (0.3 g) in a mixture of ethanol (60 ml), water (30 ml) and tetrahydrofuran (20 ml) was portionwise added the iron powder (3 g) at 80° C. with stirring. The mixture was refluxed for 2.5 hours with stirring. The reaction mixture was filtered by suction and the filtrate was concentrated under reduced pressure. The residue was triturated with water, the precipitates were collected by filtration, washed with water and dried in vacuo to give 2-acetylamino-5-(4-aminophenylthio)thiazole (2.0 g, yield: 79.5%).

mp: 255°–257° C. (dec.) IR (Nujol): 3450, 3375, 1680, 1620, 1595, 1380, 1300 cm$^{-1}$ NMR (DMSO-d$_6$, 60 MHZ, ppm): 2.17 (3H, s), 5.40 (2H), s), 6.60 (2H, d, J=9 Hz), 7.20 (2H, d, J=9 Hz), 7.58 (1H, s), 12.15 (1H, s)

EXAMPLE 18

A solution of 2-acenylamino-5-(4-aminophenylthio)thiazole (2.4 g) in a mixture of acetic acid (20 ml) and 6N-aqueous hydrochloric acid (5 ml) was refluxed for 4 hours with stirring. The reaction mixture was poured into ice-water and the solution was adjusted to pH 10 using 1N-aqueous sodium hydroxide with stirring under ice cooling. The precipitates were collected by filtration, washed with water and dried in vacuo to give 2-amino-5-(4-aminophenylthio)thiazole (1.70 g, yield: 81.5%).

IR (Nujol): 3400, 3300, 3150, 1630, 1600, 1515, 1380 cm$^{-1}$ NMR (DMSO-d$_6$, 60 MHZ, ppm): 5.27 (2H, s), 6.60 (2H, d, j=9 Hz), 7.10 (2H, d, J=9 Hz), 7.17 (1H, s), 7.27 (2H, s) Mass: M$^{+1}$ 224, M 223, m/e 191, 164, 136, 125

EXAMPLE 19

To a solution of 2-amino-5-(4-aminophenylthio)thiazole (4.0 g) in a mixture of chloroform (140 ml) and N,N-dimethylformamide (20 ml) was dropwise added the solution of 3-chloroperbenzoic acid (4.65 g) in chloroform (50 ml) at 5° C. with stirring. The mixture was stirred at 5° C. for 4 hours. The precipitates were collected by filtration, washed with 10% aqueous sodium bicarbonate and water. The solid was dried in vacuo to give 2-amino-5-(4-aminophenylsulfinyl)thiazole (3.75 g, yield: 87.5%).

mp: 173°–175° C. IR (Nujol): 3500, 3350, 3225, 1640, 1595, 1525, 1380, 1320, 1225 cm$^{-1}$ NMR (DMSO-d$_6$, 90 MHZ, ppm): 5.67 (2H, s), 6.97 (2H, d, J=9 Hz), 7.23 (2H, d, J=9 Hz), 7.50 (1H, s), 7.62 (2H, s) Mass: M$^{+1}$ 240, M 239, m/e 223, 191, 147, 140

EXAMPLE 20

To a solution of 2-acetylamino-5-(4-aminophenylthio)thiazole (6.6 g) in a mixture of dichloromethane (300 ml) and N,N-dimethylformamide (50 ml) was dropwise added the solution of 3-chloroperbenzoic acid (5.9 g) in dichloromethane (100 ml) at 5° C. with stirring. The mixture was stirred at 5° C. for 2 hours with stirring. The reaction mixture was concentrated under reduced pressure and the residue was poured into 10% aqueous sodium bicarbonate. The solution was extracted with a mixture of tetrahydrofuran and ethyl acetate (1:1), washed with saturated aqueous sodium chloride and dried over magnesium sulfate. The solvent was concentrated under reduced pressure to give 2-acetylamino-5-(4-aminophenylsulfinyl)thiazole (5.0 g, yield: 71.1%).

mp: 194°–196° C. (dec.) IR (Nujol): 3350, 3175, 1710, 1630, 1695, 1550, 1380, 1300, 1230 cm$^{-1}$ NMR (DMSO-d$_6$, 60MHZ, ppm): 2.17 (3H, s), 5.80 (2H, br s), 6.70 (2H, d, J=9 Hz), 7.37 (2H, d, J=9 Hz), 7.9 (1H, s) Mass: M$^{+}$282, M 281, m/e 265, 234, 222, 191

EXAMPLE 21

A mixture of 2-acetylamino-5-(4-aminophenylsulfinyl)thiazole (5.0 g) in a mixture of aqueous 6N-hydrochloric acid (10 ml) and acetic acid (35 ml) was refluxed for 3.5 hours with stirring. The reaction mixture was diluted with water and adjusted to pH 8 using aqueous sodium carbonate under ice cooling. The precipitates were collected by filtration, washed with water and dried in vacuo to give 2-amino-5-(4-aminophenylsulfinyl)thiazole (4.5 g, yield: 100%).

mp: 205°–208° C (dec.) (DMSO-d$_6$, 60 MHZ, ppm): 5.27 (2H, s), 6.55 (2H, d, j=8 Hz), 6.67 (2H, d, J=8 Hz), 7.17 (1H, s), 7.42 (2H, s) Mass: m/e 223, 191, 124, 99

EXAMPLE 22

A mixture of 2-acetylamino-5-chlorothiazole (5.3 g), 4-mercaptopyridine (3.4 g) and potassium carbonate in N,N-dimethylformamide (50 ml) was heated at 120° C. for 2.5 hours with stirring. The reaction mixture was concentrated under reduced pressure and the residue was triturated with water. The precipitates were collected by filtration, washed with water and dried in vacuo to give 2-acetylamino-5-(4-pyridylthio)thiazole (6.3 g, yield: 83.7%). IR (Nujol): 3150, 1680, 1580, 1300 cm$^{-1}$ NMR (DMSO-d$_6$, 90 MHZ, ppm): 2.23 (3H, s), 7.10 (2H, d, J=6 Hz), 7.80 (1H, s), 8.40 (2H, d, J=6 Hz), 11.90 (1H, br s)

EXAMPLE 23

A mixture of 2-acetylamino-5-(4-pyridylthio)thiazole (4.7 g), acetic acid (35 ml) and 6N-aqueous hydrochloric acid (10 ml) was refluxed for 2 hours with stirring. The reaction mixture was concentrated under reduced pressure and the residue was dissolved in water. The solution was adjusted pH 8.5 using aqueous sodium bicarbonate under ice cooling. The precipitates were collected by flirtation, washed with water and dried in vacuo to give 2-amino-5-(4-pyridylthio)thiazole (2.7 g, yield: 69.5%).

mp: 180°–185° C. (dec.) IR (Nujol): 3270, 3150, 1630, 1580, 1380 cm$^{-1}$ ′ NMR (DMSO-d$_6$, 90 MHZ, ppm): 7.13 (2H, d j=6 Hz), 7.30 (1H, S), 7.60 (2H, s), 8.40 (2H, d, J=6 Hz) Mass: M$^{+}$210, M 209, m/e 188, 150, 131, 99

EXAMPLE 24

To a mixture of 2-amino-5-(4-pyridylthio)thiazole (4.0 g) in a mixture of chloroform (300 ml) and N,N-dimethylformamide (10 ml) was added dropwise the solution of 3-chloroperbenzoic acid (4.5 g) in chloroform (100 ml) at 5° C. with stirring. The mixture was stirred at 5° C. for 26 hours under ice cooling. The reaction mixture was washed with aqueous sodium bicarbonate and water and dried over magnesium sulfate. The solvent was concentrated under reduced pressure to give solid. The solid was subject to column chromatography on silica gel (silica gel 60, 70–230 mesh; Merck: 250 g) and eluted with a mixture of chloroform and methanol (10:1). The fractions containing the objective compound were combined and concentrated under reduced pressure to give 2-amino-5-(4-pyridylsulfinyl)thiazole (2.5 g, yield: 58.1%).

mp: 193°–195° C. IR (Nujol): 3350, 3250, 1610, 1575, 1525, 1280, 1220 cm$^{-1}$ NMR (DMSO-d$_6$, 60 MHZ, ppm): 7.62 (2H, d, J=6 Hz), 7.87 (1H, s), 7.97 (2H, s), 8.80 (2H, d, J=6 Hz) Mass: M 225, m/e 209, 177, 147, 131

EXAMPLE 25

A mixture of 2-acetylamino-5-(4-nitrophenylthio)thiazole (4.0 g) in a mixture of acetic acid (30 ml) and aqueous 6N hydrochloric acid (9 ml) was refluxed for 3 hours with stirring. The reaction mixture was concentrated under reduced pressure and the residue was dissolved in water. The solution was adjusted to pH 8.5 using aqueous sodium bicarbonate. The precipitates were collected by filtration, washed with water and dried in vacuo to give 2-amino-5-(4-nitrophenylthio)thiazole (2.6 g, yield: 76.5%).

mp 162°–164° C. IR (Nujol): 3420, 3270, 1680, 1595, 1580, 1530, 1335, 1215 cm$^{-1}$ NMR (DMSO-d$_6$, 60 MHZ, ppm): 7.30 (2H, d, j=8 Hz), 7.40 (1H, s), 7.50 (2H, s), 8.20 (2H, d, J=8 Hz) Mass: M$^{+}$254, M 253, m/e 223, 191, 164, 149, 121, 99

EXAMPLE 26

To a mixture of 2-amino-5-(4-nitrophenylthio)thiazole (2.6 g) and pyridine (1 g) in N,N-dimethylformamide (30 ml) was added dropwise the propionylchloride (1.1 g) at 5° C. under ice cooling with stirring. The mixture was stirred at 5° C. for 3.5 hours. The reaction mixture was poured into ice water and the mixture was adjusted to pH 8 using aqueous sodium bicarbonate. The precipitates were collected by filtration, washed with water and dried in vacuo to give 2-propionylamino-5-(4-nitrophenylthio)thiazole (2.5 g, yield: 78.7%).

mp: 227°–229° C. (dec.) IR (Nujol): 3150, 1710, 1595, 1580, 1555, 1505, 1340, 1180 cm$^{-1}$ NMR (DMSO-d$_6$, 60 MHZ, ppm): 1.20 (3H, t, J=8 Hz), 2.6 (2H, q, J=8 Hz), 7.45 (2H, d, J=8 Hz), 7.92 (1H, s), 8.23 (2H, d, J=8 Hz) Mass: M$^{+1}$ 310, M 309, m/e 280, 252, 222

EXAMPLE 27

To a mixture of 2-propionylamino-5-(4-nitrophenylthio)thiazole (3 g), and ammonium chloride (1 g) in a mixture of ethanol (100 ml), water (30 ml) and tetrahydrofuran (70 ml) was portionwise added the iron powder at 80° C. with stirring. The mixture was refluxed for 2 hours with stirring. The reaction mixture was filtered by suction and the filtrate was concentrated under reduced pressure. The residue was triturated with water, the precipitates were collected by filtration and washed with water to give solid. The solid was recrystallized from ethanol to give 2-propionylamino-5-(4-aminophenylthio)thiazole (2.6 g, yield: 96.3%).

mp: 185°–187° C. NMR (DMSO-$d_6$, 60 MHZ ppm): 1.30 (3H, t, J=7 Hz), 2.50 (2H, q, J=7 Hz), 5.50 (2H, br s), 6.60 (2H, d, J=8 Hz), 7.23 (2H, d, J=8 Hz), 7.60 (1H, s) Mass: $M^{+1}$ 280, M 279, m/e 264, 250, 222, 205

EXAMPLE 28

A mixture of 2-acetylamino-5-chlorothiazole (5.3 g), 2-mercaptopyridine (3.5 g) and potassium carbonate (6.2 g) in N,N-dimethylformamide (50 ml) was heated at 130° C. for 3.5 hours with stirring. The reaction mixture was concentrated under reduced pressure and the residue was triturated with water. The precipitates were collected by filtration, washed with water and dried in vacuo to give 2-acetylamino-5-(2-pyridylthio)thiazole (5.70 g, yield: 76.0%).

mp: 185°–188° C. (dec.) IR (Nujol): 3150, 1695, 1575, 1300, 1280, 1230 cm$^{-1}$ NMR (DMSO-$d_6$, 60 MHZ, ppm): 2.20 (3H, s), 7.00–7.40 (2H, m), 7.70–7.90 (2H, m), 8.50 (1H, m), 12.40 (1H, s) Mass: $M^{+1}$ 252, M 251, m/e 209, 176, 167

EXAMPLE 29

A mixture of 2-acetylamino-5-(2-pyridylthio)thiazole (5.0 g) in a mixture of acetic acid (50 ml) and aqueous N-hydrochloric acid (10 ml) was refluxed for 2 hours with stirring. The reaction mixture was concentrated under reduced pressure and the residue was dissolved in water. The solution was adjusted to pH 8.5 using aqueous bicarbonate, and then the mixture was extracted with ethyl acetate. The organic layer was washed with water and dried over magnesium sulfate. The solvent was concentrated under reduced pressure and the residue was triturated with a solution of hydrochloric acid in ethanol The precipitates were collected by filtration, washed with isopropyl ether and dried in vacuo to give 2-amino-5-(2-pyridylthio)thiazole dihydrochloride (4.60 g, yield: 85.8%).

mp: 220°–225° C. (dec.) IR (Nujol): 2550–2300, 1620, 1595 cm$^{-1}$ NMR (DMSO-$d_6$, 60 MHZ, ppm): 7.20–7.60 (2H, m), 7.70–8.00 (4H m), 8.55 (1H, m) 10.50 (3H, br s) Mass: m/e 209 (free), 187, 167, 123

EXAMPLE 30

To a solution of 2-amino-5-(2-pyridylthio)thiazole dihydrochloride (4.0 g) in chloroform (100 ml) was dropwise added the solution of 3-chloroperbenzoic acid (5.0 g) in chloroform (100 ml) at 5° C. with stirring. The mixture was stirred at 5° C. for 1.5 hours. The reaction mixture was washed with aqueous sodium bicarbonate and dried over magnesium sulfate. The solvent was concentrated under reduced pressure to give solid. The solid was subjected to column chromatography on silica gel (silica gel 60, 70–230 mesh; Merck: 100 g) and eluted with a mixture of chloroform and methanol (10:1). The fractions containing the objective compound were combined and concentrated under reduced pressure to give 2-amino-5-(2-pyridylsulfinyl)thiazole (3.4 g, yield: 78.9%).

mp: 200°–202° C. (dec.) IR (Nujol): 3300, 3150, 1630, 1575, 1270, 1225 cm$^{-1}$ NMR (DMSO-$d_6$, 90 MHZ, ppm): 7.40–7.60 (1H, m), 7.70 (1H, s), 7.73 (2H, s), 7.90–8.20 (2H, m), 8.60 (1H, m) Mass: M 225, m/e 209, 147, 115

EXAMPLE 31

To a solution of 2-amino-5-(2-pyridylthio)thiazole (5.7 g) in chloroform (450 ml) was dropwise added the solution of 3-chloroperbenzoic acid (15 g) in chloroform (100 ml) at 5° C. with stirring. The mixture was stirred at room temperature for 16 hours. The reaction mixture was washed with aqueous sodium bicarbonate and dried over magnesium sulfate. The solvent was concentrated under reduced pressure to give 2-amino-5-(2-pyridylsulfonyl)thiazole (2.2 g, yield: 33%).

mp: 178°–182° C. (dec.) IR (Nujol): 3375, 3300, 3150, 1645, 1610, 1525, 1320, 1220 cm$^{-1}$ NMR (DMSO-$d_6$, 60 MHZ, ppm): 7.55–7.80 (2H, m), 8.00–8.30 (4H, m), 8.77 (1H, m) Mass: $M^{+1}$ 242, M 241, m/e 177, 156, 135

EXAMPLE 32

A mixture of 2-acetamido-5-chlorothiazole (14.3 g), 2-mercaptopyrimidine (10 g) and potassium carbonate anhydrous (22.4 g) in N,N-dimethylformamide (280 ml) was stirred at 150° C. an hour. The reaction mixture was poured into water with stirring under ice cooling. The mixture was extracted with ethyl acetate, washed with water and dried over magnesium sulfate. The organic layer was concentrated under reduced pressure to give solid. The solid was triturated with water, and the precipitates were collected by filtration, washed with water and dried in vacuo no give 2-acetamido-5-(2-pyrimidinylthio)thiazole (12.30 g, yield: 60.2%). mp: 225° C. (dec.) IR (Nujol): 3170, 1645, 1555, 1310 cm$^{-1}$ NMR (DMSO-$d_6$, 60 MHZ, ppm): 2.20 (3H, s), 7.33 (1H, t, j=4 Hz), 7.70 (1H, s), 8.68 (2H, d, J=4 Hz), 12.33 (1H, br s) Mass: $M^{+2}$ 254, $M^{+1}$ 253, M 252, m/e 210, 168

EXAMPLE 33

Starting from 2-acetamido-5-(2-pyrimidinylthio)thiazole, 2-amino-5-(2-pyrimidinylthio)thiazole (2.32 g, yield: 22.0%) was obtained according to a similar manner to that of Example 40.

mp: 175°–177° C. IR (Nujol): 3270, 3100, 1655, 1565, 1555, 1540 cm$^{-1}$ NMR (DMSO-$d_6$, 60 MHZ, ppm): 7.13–7.57 (4H, m), 8.40–8.77 (2H, m) Mass: $M^+$212, $M^{+1}$ 211, M 210, m/e 168, 124

EXAMPLE 34

A mixture of 2-acetylamino-5-chlorothiazole (5.3 g), 1-methyl-2-mercaptoimidazole (3.6 g) and potassium carbonate (6.2 g) in N,N-dimethylformamide (50 ml) was heated at 130° C. for 5.5 hours with stirring. The reaction mixture was concentrated under reduced pressure and the residue was triturated with water. The precipitates were collected by filtration washed with water and dried in vacuo to give 2-acetylamino-5-(1-methylimidazol-2-ylthio)thiazole (6.95 g, yield: 91.2%).

mp: 155°–160° C. (dec.) IR (Nujol): 3400, 1690, 1565, 1300 cm$^{-1}$ NMR (DMSO-$d_6$, 90 MHZ, ppm): 2.10 (3H, s), 3.70 (3H, s), 6.90 (1H, s), 7.26 (1H, s), 7.60 (1H, s) Mass: $M^{+1}$ 255, M 254, m/e 212, 179, 170, 114

EXAMPLE 35

A solution of 1-acetylamino-5-(1-methylimidazol-2-ylthio)thiazole (7.0 g) in a mixture of acetic acid (100 ml) and aqueous 6N-hydrochloric acid (20 ml) was refluxed for 3.5 hours with stirring. The reaction mixture was concentrated under reduced pressure and the residue was adjusted to pH 8 using aqueous sodium bicarbonate under ice cooling. The precipitates were collected by filtration, washed with water and dried in vacuo to give 2-amino-5-(1-methylimidazol-2-ylthio)thiazole (4.9 g, yield: 83.9%).

mp: 180°–190° C. (dec.) IR (Nujol): 3300, 3150, 1620, 1530, 1280, 1220 cm$^{-1}$ NMR (DMSO-$d_6$, 60 MHZ, ppm): 3.77 (3H, s), 7.03 (1H, s), 7.25 (1H, s), 7.37 (1H, s) Mass: M$^{+1}$ 213, M 212, m/e 179, 170, 126, 114

EXAMPLE 36

A solution of 2-acetamido-5-(4-aminophenylthio)thiazole (3.2 g) in pyridine (64 ml) was added menhanesulfonyl chloride (1.52 g) at 5° C. with stirring. The reaction mixture was stirred for 3 hours at 5° C. and concentrated in vacuo to give solid. The solid was subject to column chromatography on silica gel (silica gel, 70–230 mesh; Merck: 200 g) and eluted with a mixture of chloroform and methanol (50:1) and eluted with a mixture of chloroform and methanol (20:1). The fractions containing the objective compound were combined and evaporated to dryness in vacuo to give 2-acetamido-5-(4-methanesulfonylaminophenylthio)thiazole (4.0 g, yield: 96.6%).

mp: 236°–239° C. IR (Nujol): 3250, 3150, 1695, 1565, 1495, 1330 cm$^{-1}$ NMR (DMSO-$d_6$, 60 MHZ, ppm): 2.16 (3H, s), 3.30 (3H, s), 7.20–7.30 (5H, m), 7.73 (1H, s), 8.10 (1H, s) Mass: M$^+$343, m/e 342, 301, 264, 222

EXAMPLE 37

Starting from 2-acetamido-5-(4-methanesulfonylaminophenylthio)thiazole, 2-amino-5-(4-methanesulfonylaminophenylthio)thiazole (2.28 g, yield: 64.9%) was obtained according to a similar manner to that of Example 40.

mp: 185°–187° C. IR (Nujol): 3430, 3260, 1610, 1510, 1320 cm$^{-1}$ NMR (DMSO-$d_6$, 60 MHZ, ppm): 3.00 (3H, s), 7.20–7.37 (5H, m), 7.47 (2H, br s), 9.76 (1H, br s) Mass: M$^{+1}$ 302, M$^{+1}$ 301, m/e 222, 190

EXAMPLE 38

To a mixture of 2-amino-5-(4-pyridylthio)thiazole (2.5 g) and pyridine (3 g) in N,N-dimethylformamide (25 ml) was added dropwise the 4-fluorobenzoyl chloride (2.7 g) at 5° C. under ice cooling with stirring. The mixture was stirred at 5° C. for 4 hours under ice cooling. The reaction mixture was concentrated under reduced pressure and the residue was triturated with water. The precipitates were collected by filtration, washed with water and dried in vacuo to give 2-(4-fluorobenzoylamino)-(4-pyridylthio)thiazole (2.5 g, yield: 63.1%).

mp: 220°–225° C. (dec.) IR (Nujol): 3150, 1670, 1605, 1587, 1550, 1295, 1230 cm$^{-1}$ NMR (DMSO-$d_6$, 60 MHZ, ppm): 7.10–7.67 (4H, m), 7.95 (1H, s), 8.10–8.60 (4H, m), 12.85 (1H, s) Mass: M$^{+1}$ 332, M 331, m/e 209, 123, 95

EXAMPLE 39

A mixture of salt of potassium 2,4-difluorothiophenol (20 g), 2-acetamido-5-chlorothiazole (21 g) and potassium carbonate anhydrous (29.8 g) in N,N-dimethylformamide (400 ml) was stirred at 130° C. for 7 hours. The reaction mixture was concentrated under reduced pressure. The residue was triturated with water and the precipitates were collected by filtration, washed with water and dried in vacuo to give solid. The solid was subjected to column chromatography on silica gel (silica gel, 70–230 mesh; Merck: 750 g) and eluted with a mixture of chloroform and methanol (50:1). The fractions containing the objective compound were combined and evaporated to dryness in vacuo to give 2-acetamido-5-(2,4-difluorophenylthio)thiazole (11.91 g, yield: 38.5%).

mp: 156°–170° C. (dec.) IR (Nujol): 3160, 3060, 1695, 1585, 1560, 1295 cm$^{-1}$ NMR (DMSO-$d_6$, 60 MHZ, ppm): 2.20 (3H, s), 6.90–7.90 (4H, m), 12.27 (1H, br s) Mass: M 286, m/e 270, 243

EXAMPLE 40

A mixture of 2-acetamido-5-(2,4difluorophenylthio)thiazole (14.8 g) in a mixture of ethanol (150 ml) and concentrated hydrochloric acid (15 ml) was refluxed for 1.5 hours with stirring. The reaction mixture was concentrated under reduced pressure and the residue was dissolved in water. The solution was adjusted to pH 12 using aqueous sodium hydroxide with stirring under ice-cooling. The mixture was extracted with ethyl acetate, washed with water and dried over magnesium sulfate. The organic layer was concentrated under reduced pressure to give solid. The solid was subjected to column chromatography on silica gel (silica gel, 230–400 mesh, Nakarai) (300 g) and eluted with a mixture of chloroform and methanol (100:1). The fractions containing the objective compound were combined and evaporated to dryness in vacuo to give 2-amino-3-(2,4-difluorophenylthio)thiazole (6.26 g, yield: 49.6%).

mp: 116°–117° C. IR (Nujol): 3410, 3090, 1625, 1600, 1515 cm$^{-1}$ NMR (DMSO-$d_6$, 60 MHZ, ppm): 7.07–7.76 (6H, m) Mass: M$^{+1}$ 260, m/e 244, 212

EXAMPLE 41

Starting from 2-amino-5-(2,4-difluorophenylthio)thiazole, 2-amino-5-(2,4-difluorophenylsulfinyl)thiazole (2.37 g, yield: 65.4%) was obtained according to a similar manner to that of Example 30.

mp: 171°–172° C. IR (Nujol): 3300, 3100, 1635, 1605, 1600 cm$^{-1}$ NMR (DMSO-$d_6$, 90 MHZ, ppm): 7.23–8.00 (6H, m) Mass: M$^{+1}$ 260, m/e 244, 212

EXAMPLE 42

A mixture of 4-chloromethy-2-formylaminothiazole (1.86 g), 4-mercaptopyridine (1.23 g) and potassium carbonate (1.8 g) in N,N-dimethylformamide (20 ml) was heated at 100° C. for 2 hours with stirring. The reaction mixture was concentrated under reduced pressure and the residue was triturated with water. The precipitates were collected by filtration, washed with water and dried in vacuo to give 2-formylamino-4-(4-pyridylthiomethyl)thiazole (1.7 g, yield: 68.0%).

mp: 182°–184° C. IR (Nujol): 1675, 1650, 1585, 1560, 1270 cm$^{-1}$ NMR (DMSO-$d_6$, 60 MHZ, ppm): 4.30 (2H, s), 7.15 (1H, s), 7.33 (2H, d, J=6 Hz), 8.33 (2H, d, J=6 Hz), 8.45 (1H, s) Mass: M$^{+1}$ 252, M 251, m/e 223, 155, 141, 113

EXAMPLE 43

A mixture of 2-formylamino-4-(4-pyridylthiomethyl)thiazole (1.6 g) and N-chlorosuccinimide (1.5 g) in acetic acid (25 ml) was heated at 40°–50° C. for 5 hours with stirring and then the mixture was allowed to stand at room temperature for 16 hours. The reaction mixture was concentrated under reduced pressure and the residue was triturated with aqueous sodium bicarbonate. The precipitates were collected by filtration washed with water and dried in vacuo to give 5-chloro-2-formylamino-4-(4-pyridylthiomethyl)thiazole (0.85 g, yield: 46.8%).

mp: 200°–203° C. (dec.) IR (Nujol): 1680, 1665, 1587, 1300 cm$^{-1}$ NMR (DMSO-d$_6$, 60 MHZ, ppm): 4.37 (2H, s), 7.40 (2H, d, J=6 Hz), 7.47 (2H, d, J=6 Hz), 8.53 (1H, s), 12.50 (1H, s) Mass: M$^{+3}$ 288, M$^{+2}$ 287, M$^{+1}$ 286, M 285, m/e 256, 250, 175, 147

EXAMPLE 44

A solution of 5-chloro-2-formylamino-4-(4-pyridylthiomethyl)thiazole (4.9 g) in a mixture of ethanol (25 ml), tetrahydrofuran (20 ml) and concentrated hydrochloric acid (7 ml) was stirred at room temperature for 4 hours. The reaction mixture was concentrated under reduced pressure and the residue was dissolved in water. The solution was adjusted to pH 8 using aqueous sodium bicarbonate under ice-cooling. The precipitates were collected by filtration, washed with water and dried in vacuo to give 2-amino-5-chloro-4-(4-pyridylthiomethyl)thiazole (0.26 g, yield: 56.6%).

IR (Nujol): 3350, 3250, 1685, 1530 cm$^{-1}$ NMR (DMSO-d$_6$, 60 MHZ, ppm): 4.13 (2H, s), 7.33 (2H, d, J=6 Hz), 7.43 (2H, s), 8.50 (2H, d, J=6 Hz) Mass: M$^{+2}$ 259, M$^{+1}$ 258, M 257, m/e 220, 147, 111

EXAMPLE 45

A mixture of 4-chloromethyl-2-formylaminothiazole (1.76 g), 4-nitrothiophenol (1.7 g) and potassium carbonate (1.8 g) in N,N-dimethylformamide (20 ml) was heated at 100° C. with stirring. The reaction mixture was poured into ice-water and stirred at 5° C. for an hour. The precipitates were collected by filtration, washed with water and dried in vacuo to give 2-formylamino-4-(4-nitrophenylthiomethyl)thiazole (2.3 g, yield: 78%).

mp: 158°–160° C. IR (Nujol): 3500, 1680, 1595, 1550, 1330 cm$^{-1}$ NMR (DMSO-d$_6$, 60 MHZ, ppm): 4.40 (2H, s), 7.13 (1H, s), 7.56 (2H, d, J=8 Hz), 8.10 (2H, d, J=8 Hz), 8.50 (1H, s) Mass: M 295, m/e 265, 141, 113

EXAMPLE 46

To a mixture of 2-formylamino-4-(4-nitrophenylthiomethyl)thiazole (2.2 g) and ammonium chloride (0.5 g) in a mixture of tetrahydrofuran (30 ml), ethanol (50 ml) and water (10 ml) was added portionwise the iron powder at 80° C. with stirring. The mixture was refluxed for 2 hours with stirring. The reaction mixture was filtered by suction and the residue was triturated with water. The precipitates were collected by filtration, washed with water and dried in vacuo to give 2-formylamino-4-(4-aminophenylthiomethyl)thiazole (1.6 g, yield: 81%).

mp: 180°–182° C. IR (Nujol): 3350, 3300, 1680, 1625, 1600, 1325, 1290 cm$^{-1}$ NMR (DMSO-d$_6$, 60 MHZ, ppm): 4.00 (2H, s), 5.23 (2H, s), 6.57 (2H, d, J=8 Hz), 6.83 (1H, s), 7.10 d, J=8 Hz), 8.50 (1H, s) Mass: M$^{+1}$ 266, M 265, m/e 237,205, 141, 124

EXAMPLE 47

A mixture of acetic anhydride (1.84 g) and formic acid (0.9 g) was heated at 50° C. for 0.5 hours with stirring. The solution was cooled at room temperature ant to the solution was added the 2-formylamino-4-(4-amino-phenylthiomethyl)thiazole (1.6 g). The mixture was stirred at room temperature for 6.5 hours and then the mixture was poured into ice-water. The precipitates were collected by filtration, washed with water and dried in vacuo to give 2-formylamino-4-(4-formylaminophenylthiomethyl)thiazole (1.7 g, yield: 96.7%).

mp: 195°–197° C. (dec.) IR (Nujol): 3150, 1680, 1660, 1595, 1525, 1310, 1290 cm$^{-1}$ NMR (DMSO-d$_6$, 60 MHZ, ppm): 4.30 (2H, s), 7.10 (1H, s), 7.47 (2H, d, J=8 Hz), 7.73 (2H, d, J=8 Hz), 8.40 (1H, s), 8.60 (1H, s), 10.33 (1H, s), 12.20 (1H, s) Mass: M$^{+1}$ 294, M 293, m/e 265, 153, 141, 113

EXAMPLE 48

To a solution of 2-formylamino-4-(4-formylaminophenylthiomethyl)thiazole (2.9 g) in acetic acid (30 ml) was portionwise added N-chlorosuccinimide at 50° C. with stirring. The mixture was heated at 50° C. with stirring. The reaction mixture was concentrated under reduced pressure and the residue was triturated with water. The mixture was extracted with a mixture of ethyl acetate and tetrahydrofuran (1:1), washed with water and dried over magnesium sulfate. The solvent was concentrated under reduced pressure to give solid. The solid was subjected to column chromatography on silica gel (silica gel 60, 70–230 mesh; Merck: 150 g) and eluted with a mixture of chloroform and methanol (10:1). The fractions containing the objective compound were combined and concentrated under reduced pressure to give 5-chloro-2-formylamino 4(4-formylaminophenylthiomethyl)thiazole (2.0 g yield: 61.2%).

mp: 130°–150° C. (dec.) IR (Nujol): 3350, 3200, 1710, 1690–1640, 1590 cm$^{-1}$ NMR (DMSO-d$_6$, 90 MHZ, ppm): 4.80 (2H, s), 7.26 (2H, d, J=8 Hz) 7.56 (2H, d, J=8 Hz) 8.25 (1H, s), 8.50 (1H, s), 10.23 (1H, s), 12.57 (1H, s) Mass: M 327, m/e 298, 292, 263, 234, 204

EXAMPLE 49

A solution of 5-chloro-2-formylamino-4-(4formylaminophenylthiomethyl thiazole (3.5 g) in a mixture of concentrated hydrochloric acid (9 ml), methanol (30 ml) and tetrahydrofuran (30 ml) was stirred at room temperature for 4 hours. The reaction mixture was concentrated under reduced pressure and the residue was dissolved into water. The solution was adjusted to pH 8 using aqueous sodium bicarbonate with stirring under ice cooling. The precipitates were collected by filtration washed with water and dried in vacuo to give solid. The solid was subjected to column chromatography on silica gel (silica gel 60, 70–230 mesh; Merck: 150 g) and eluted with a mixture of chloroform and methanol (10:1). The fractions containing the objective compound were combined and concentrated under reduced pressure to give 2-amino-4-(4-aminophenylthiomethyl)-5-chlorothiazole (2.3 g, yield: 79.3%).

mp: 158°–163° C. (dec.) IR (Nujol): 3325, 3200, 3150, 1620, 1595, 1495, 1325, 1290 cm$^{-1}$ NMR (DMSO-d$_6$, 60 MHZ, ppm): 4.33 (2H, s), 5.50 (2H, br s), 6.60 (2H, d, J=8 Hz), 7.10 (2H, d, J=8 Hz), 7.25 (2H, br s) Mass: M 271, m/e 267, 236, 221, 204, 124

EXAMPLE 50

A mixture of 2-acetylamino-5-chloro-4-hydroxymethylthiazole (1 g), 4-mercaptopyridine (0.6 g) and potassium carbonate (1 g) in N,N-dimethylformamide (20 ml)

was heated at 110° C. for 8 hours with stirring. The reaction mixture was poured into ice water and filtered by suction. The filtrate was extracted with a mixture of ethyl acetate and tetrahydrofuran (1:1) and dried over magnesium sulfate. The solvent was concentrated under reduced pressure to give solid. The solid was subjected to column chromatography on silica gel (silica gel 60, 70–230 mesh; Merck: 75 g) and eluded with a mixture of chloroform and methanol (10:1l). The fractions containing the objective compound were combined and concentrated under reduced pressure to give 2-acetylamino-4-hydroxymethyl-5-(4-pyridylthio)-thiazole (0.90 g, yield: 64.3%).

mp: 220°–222° C. (dec.) NMR (DMSO-$d_6$, 90 MHZ, ppm): 2.16 (3H, s), 4.40 (2H, d, J=6 Hz), 5.13 (1H, t, J=6 Hz), 7.05 (2H, d, J=6 Hz), 8.30 (2H, d, J=6 Hz), 12.43 (1H, s) Mass: M$^{+1}$ 282, M 281, m/e 239, 220, 205, 188

EXAMPLE 51

A mixture of 2-acetylamino-4-hydroxymethyl-5-(4-pyridylthio)thiazole (3.0 g) in a mixture of concentrated hydrochloric acid (8 ml) and ethanol (100 ml) was refluxed for 2.5 hours with stirring. The reaction mixture was concentrated under reduced pressure and the residue was triturated with acetone. The precipitates were collected by filtration, washed with isopropyl ether and were recrystallized from a mixture of ethanol and isopropyl ether to give 2-amino-4-hydroxymethy-5-(4-pyridylthio)thiazole dihydrochloride (2.5 g, yield: 75.3%).

mp: 231°–237° C. (dec.) IR (Nujol): 3350, 2300, 1610, 1560 cm$^{-1}$ NMR DMSO-$d_6$, 90 MHZ, ppm): 4.30–4.55 (3H, m), 7.80 (2H, d, J=6 Hz), 8.65 (2H, d, J=6 Hz), 8.83 (4H, br s) Mass: M 239, m/e 222, 210, 188

EXAMPLE 52

Starting from 2-amino-5-(4-pyridylthio)thiazole 2-amino-5-(4-pyridylsulfonyl)thiazole (0.73 g, yield: 17.1%) was obtained according to a similar manner to that of Example 31.

mp: 217° C. (dec.) IR (Nujol): 3260, 3100, 1620, 1580, 1525 cm$^{-1}$ NMR (DMSO-$d_6$, 90 MHZ, ppm): 7.73–7.86 (3H, m), 8.20 (2H, br s), 8.55 (2H, d, J=6 Hz) Mass: M$^{+2}$ 243, M$^{+1}$ 242, M$^{+}$241, m/e 209, 195

EXAMPLE 53

A mixture of 2-amino-5-(4-aminophenylthio)thiazole, (4.0 g) in a mixture of acetic acid (40 ml) and acetic anhydride (2.2 g) was stirred at room temperature for 4 hours. The reaction mixture was concentrated under reduced pressure and the residue was triturated with aqueous sodium bicarbonate. The precipitates were collected by filtration, washed with water and dried in vacuo to give solid. The solid was subjected to column chromatography on silica gel (silica gel 60, 70–230 mesh; Merck: 150 g) and eluted with a mixture of chloroform and methanol (10:1). The fractions containing the objective compound were combined and concentrated under reduced pressure to give 2-amino-5-(4-acetylaminophenylthio)thiazole (2.1 g, yield: 44.2%).

mp: 240°–245° C. (dec.) IR (Nujol): 3400, 3325, 3200, 1660, 1605, 1595, 1320 cm$^{-1}$ NMR (DMSO-$d_6$, 60 MHZ, ppm): 2.10 (3H, s), 7.26 (2H, d, J=8 Hz), 7.30 (1H, s), 7.50 (2H, s), 7.67 (2H, d, J=8 Hz), 10.03 (1H, s) Mass: M$^{+1}$ 266, M 265, m/e 223, 207, 190

EXAMPLE 54

To a mixture of 2-amino-5-(4-methanesulfonylaminophenylthio)thiazole (2.0 g) in chloroform (100 ml) was added dropwise the solution of 3-chloroperbenzoic acid (1.6 g) in chloroform (50 ml) at 5° C. under ice cooling with stirring. The mixture was stirred at 5° C. for 2.5 hours. The reaction mixture was washed with aqueous sodium bicarbonate and the precipitates were collected by filtration. The solid was washed with aqueous sodium bicarbonate and water, dried in vacuo to give 2-amino-5-(4-methanesulfonylaminophenylsulfinyl)-thiazole (1.95 g, yield: 92.6%).

mp: 201°–203° C. (dec.) IR (Nujol): 3320, 3250, 3100, 1615, 1515, 1325, 1220, 1150 cm$^{-1}$ NMR (DMSO-$d_6$, 60 MHZ, ppm): 3.17 (3H, s), 7.43 (2H, d, J=8 Hz), 7.67 (2H, d, J=8 Hz), 7.73 (1H, s), 7.83 (2H, s), 10.23 (1H, s) Mass: m/e 301, 222, 190, 146, 124, 100

EXAMPLE 55

A mixture of 2-acetylamino-5-chlorothiazole (1.76 g), 4-hydroxythiophenol (1.3 g) and potassium carbonate (2 g) in N,N-dimethylformamide (30 ml) was heated at 120° C. for 2.5 hours with stirring. The reaction mixture was poured into ice water. The precipitates were collected by filtration, washed with water and dried in vacuo to give 2-acetylamino-5-(4-hydroxyphenylthio)-thiazole (1.5 g, yield: 56.6%).

mp: 265°–267° C. IR (Nujol): 3300, 3200, 1675, 1600, 1570, 1305, 1260 cm$^{-1}$ NMR (DMSO-$d_6$, 200 MHZ, ppm): 2.14 (3H, s), 6.75 (2H, d, J=9 Hz) 7.20 (2H, d, J=9 Hz) 7.63 (1H s), 9.69 (1H, s), 12.28 (1H, s) Mass: M$^{+1}$ 267, M 266, m/e 224, 191, 182, 165, 137

EXAMPLE 56

A mixture of 2-acetylamino-5-(4-hydroxyphenylthio)thiazole (1.5 g) in a mixture of ethanol (40 ml) and aqueous 6N hydrochloric acid (6 ml) was refluxed for 4.5 hours with stirring. The reaction mixture was concentrated under reduced pressure and the residue was dissolved in water. The solution was adjusted to pH 10 using aqueous sodium hydroxide under ice cooling. The precipitates were collected by filtration and recrystallized from a mixture of ethanol and water (3:1) to give 2-amino-5-(4-hydroxyphenylthio)thiazole (1.05 g, yield: 84.0%).

mp: 187°–188° C. IR (Nujol): 3450, 3350, 3200, 1625, 1600, 1500, 1320, 1245 cm$^{-1}$ NMR (DMSO-$d_6$, 200 MHZ, ppm): 6.74 (2H, d, J=9 Hz), 7.08 (2H, d, J=9 Hz), 7.13 (1H, s), 7.34 (2H, s), 9.58 (1H, s) Mass: M$^{+1}$ 225, M 224, m/e 192, 182, 165, 137

EXAMPLE 57

A mixture of 2-acetylamino-5-chlorothiazole (1.76 g), 4-methoxythiophenol (1.5 g) and potassium carbonate (2.0 g) in N,N-dimethylformamide (30 ml) was heated at 120° C. for 3.5 hours with stirring. The reaction mixture was poured into ice water and the precipitates were collected by filtration to give solid. The solid was recrystallized from ethanol to give 2-acetylamino-5-(4-methoxyphenylthio)thiazole (2.2 g, Yield: 78.6%).

mp: 190°–191° C. IR (Nujol): 3175, 1695, 1565, 1490, 1295, 1250 cm$^{-1}$ NMR (DMSO-$d_6$, 200 MHZ, ppm): 2.14 (3H, s), 3 74 (3H, s), 6.93 (2H, d, J=9 Hz), 7.25 (2H, d, J=9 Hz), 7.68 (1H, s), 12.31 (1H, s) Mass: M$^{+1}$ 281, M 280, m/e 238, 205, 196, 151

EXAMPLE 58

A mixture of 2-acetylamino-5-(4-methoxylphenylthio)thiazole (1.7 g) in a mixture of ethanol (40 ml) and aqueous 6N hydrochloric acid (6 ml) was refluxed for 4 hours with stirring. The reaction mixture was concentrated under reduced pressure and the residue was dissolved in water The solution was adjusted to pH 10 using aqueous sodium hydroxide under cooling. The precipitates were collected by filtration, washed with water and recrystallized from ethanol to give 2-amino-5-(4-methoxyphenylthio)thiazole (1.25 g, yield: 86.8%).

mp: 119°–120° C. IR (Nujol): 3400, 3275, 3100, 1635, 1595, 1520, 1460, 1240 cm$^{-1}$ NMR (DMSO-d$_6$, 200 MHZ, ppm): 3.73 (3H, s), 6.91 (2H, d, J=9 Hz), 7.17 (1H, s), 7.21 (2H, d, J=9 Hz), 7.39 (2H, s) Mass: M$^{+1}$ 239, M 238, m/e 206,196, 151

EXAMPLE 59

A mixture of 2-acetylamino-5-chlorothiazole (1.76 g), 5-mercapto-2-methyl-1,3,4-thiadiazole (1.3 g) and potassium carbonate (2.0 g) in N,N-dimethylformamide (40 ml) was heated at 120° C. for 4 hours with stirring. The reaction mixture was concentrated under reduced pressure and water was added to this residue. The mixture was extracted with a mixture of tetrahydrofuran and ethyl titrate (1:1), washed with aqueous saturated sodium chloride and dried over magnesium sulfate. The solvent was concentrated under reduced pressure to give solid. The solid was subjected to column chromatography on silica gel (silica gel 60, 70–230 mesh; Merck: 150 g) and eluted with a mixture of chloroform and methanol (10:1). The fractions containing the objective compound were combined and concentrated under reduced pressure to give 2-acetylamino-5-(2-methyl-1,3,4-thiadiazol-5-ylthio)thiazole (1.65 g, yield: 60.7%).

mp: 242°–244° C. IR (Nujol): 3250, 1695, 1550, 1300 cm$^{-1}$ NMR (DMSO-d$_6$, 200 MHZ, ppm): 2.19 (3H, s), 2.63 (3H, s), 7.95 (1H, s), 12.58 (1H, s) Mass: M$^{+1}$ 273, M 272, m/e 230, 188, 155, 131

EXAMPLE 60

A mixture of 2-acetylamino-5-(2-methyl-1,3,4-thiadiazol-5-ylthio)'thiazole (3.3 g) in a mixture of ethanol (70 ml), tetrahydrofuran (50 ml) and aqueous 6N-hydrochloric acid (200 ml) was refluxed for 6.5 hours with stirring. The reaction mixture was concentrated under reduced pressure and the residue was dissolved in water. The solution was adjusted to pH 8.5 using aqueous sodium bicarbonate and extracted with a mixture of tetrahydrofuran and ethyl acetate (1:1). The organic layer was washed with aqueous saturated sodium chloride and dried over magnesium sulfate. The organic solvent was concentrated under reduced pressure to give solid. The solid was subjected to column chromatography on silica gel (silica gel 60, 70–230 mesh; Merck: 150 g) and eluted with a mixture of chloroform and methanol (10:1). The fractions containing the objective compound were combined and concentrated under reduced pressure to give 2-amino-5-(2-methyl-1,3,4-thiadiazol-5-ylthio)thiazole (0.85 g, Yield: 58.2%).

mp: 203°–205° C. (dec.) IR (Nujol): 3450, 3300, 3100, 1640, 1520, 1485, 1220 cm$^{-1}$ NMR (DMSO-d$_6$, 200 MHZ, ppm): 2.63 (3H s), 7.42 (1H, s), 7.75 (2H, s) Mass: M$^{+1}$ 231, M 230, m/e 188, 154, 131, 113

EXAMPLE 61

A mixture of 2-acetylamino-5-chlorothiazole (1.76 g), 5-mercapto1-methyl-1H-tetrazole (1.2 g) and potassium carbonate (2 g) in N,N-dimethylformamide (40 ml) was heated at 130° C. for 3 hours with stirring. The reaction mixture was concentrated under reduced pressure and the residue was triturated with water. The precipitates were collected by filtration, washed with water and dried vacuo to give solid. The solid was subjected to column chromatography on silica gel (silica gel 60, 70–230 mesh; Merck: 150 g) and eluted with a mixture of chloroform and methanol (10:1). The fractions containing the objective compound were combined and concentrated under reduced pressure to give 2-acetylamino-5-(1-methyl-1H-tetrazol-5-ylthio)thiazole (2.1 g, yield: 82.0%).

mp: 208°–210° C. IR (Nujol): 3450, 3250, 3150, 1690, 1665, 1550, 1295, 1225 cm$^{-1}$ NMR (DMSO-d$_6$, 200 MHZ, ppm): 2.17 (3H, s), 4.11 (3H, s), 7.89 (1H, s), 12.51 (1H, s) Mass: M$^{+1}$ 257, M 256, m/e 214, 173, 159, 131

EXAMPLE 62

A mixture of 2-acetylamino-5-(1-methyl-1H-tetrazol-5-ylthio)thiazole (2.0 g) in a mixture of ethanol (20 and aqueous 6N-hydrochloric acid (5 ml) was refluxed for 4 hours with stirring. The reaction mixture was concentrated under reduced pressure and the residue was adjusted to pH 8 using aqueous sodium bicarbonate under ice cooling. The precipitates were collected by filtration, washed with water and the solid was recrystallized from ethanol to give 2-amino-5-(1-methyl -1H-tetrazol-5-ylthio)thiazole (0.81 g, yield: 48.5%).

mp: 186°–188° C. (dec.) IR (Nujol): 3400, 3250, 3150, 1612, 1510, 1490, 1215 cm$^{-1}$ NMR (DMSO-d$_6$, 200 MHZ, ppm): 4.03 (3H, s), 7.38 (1H, s), 7.63 (2H, s) Mass: M$^{+1}$ 215, M 214, m/e 131, 89, 83

EXAMPLE 63

A mixture of 2-amino-5-bromothiazole hydrochloride (2.2 g), 4-amino-2-mercaptopyrimidine (2.2 g) and potassium carbonate (6.5 g) in N,N-dimethylformamide (100 ml) was heated at 90° C. for 2.5 hours with stirring. The reaction mixture was concentrated under reduced pressure and water was added to this residue. The solution was extracted with a mixture of tetrahydrofuran and ethyl acetate (1:1), washed with aqueous saturated sodium chloride and dried over magnesium sulfate. The solvent was concentrated under reduced pressure to give solid. The solid was subjected to column chromatography on silica gel (silica gel 60, 70–230 mesh; Merck: 250 g) and eluted with a mixture of chloroform and methanol (10:1). The fractions containing the objective compound were combined and concentrated under reduced pressure to give solid. The solid was triturated with ethanol to give 2-amino-5-(4-aminopyrimidin-2-ylthio)thiazole (1.25 g, yield: 55.6%).

mp: 185°–187° C. (dec.) IR (Nujol): 3450, 3300, 3175, 3100, 1645, 1630, 1580, 1545, 1340 cm$^{-1}$ NMR (DMSO$_6$, 200 MHz, ppm): 6.16 (1H, d, J=6 Hz), 6.99 (2H, s), 7.07 (1H, s), 7.32 (2H, s), 7.86 (1H, d, J=6 Hz) Mass: M$^{+1}$ 226, M 225, m/e 183, 139

EXAMPLE 64

A mixture of 2-amino-5-bromo-4-methylthiazole hydrochloride (1.15 g), 2-mercaptopyrimidine (0.6 g) and potassium carbonate (1.7 g) in N,N-dimethylformamide (20 ml) was heated at 90° C. for 3.5 hours with stirring.

The reaction mixture was poured into ice water. The mixture was extracted with a mixture of tetrahydrofuran and ethyl acetate (1:1), washed with aqueous saturated sodium chloride and dried over magnesium sulfate. The solvent was concentrated under reduced pressure to give solid. The solid was subjected to column chromatography on silica gel (silica gel 60, 70–230 mesh; Merck: 100 g) and eluted with a mixture of chloroform and methanol (10:1). The fractions containing the objective compound were combined and concentrated under reduced pressure to give 2-amino-4-methyl-5-(2-pyrimidinylthio)thiazole (0.65 g, yield: 58.0%).

mp: 165°–170° C. (dec.) IR (Nujol): 3300, 3175, 1630, 1555, 1490, 1320 cm$^{-1}$ NMR (DMSO-d$_6$, 200 MHZ, ppm): 2.10 (3H, s), 7.24–7.33 (1H, m), 7.33 (2H, s), 8.64 (2H, d, J=5 Hz) Mass: M$^{+1}$ 225, M 224, m/e 209, 191, 182, 166, 145

EXAMPLE 65

A mixture of 2-amino-5-bromo-4-methylthiazole hydrochloride (4.5 g), 2-mercaptopyridine (2.3 g) and potassium carbonate (7.0 g) in N,N-dimethylformamide (100 ml) was heated at 90° C. for 3 hours with stirring. The reaction mixture was concentrated under reduced pressure and water was added to this residue. The mixture was extracted with a mixture of tetrahydrofuran and ethyl acetate, washed with aqueous saturated sodium chloride and dried over magnesium sulfate. The solvent was concentrated under reduced pressure to give solid. The solid was subjected to column chromatography on silica gel (silica gel 60, 70–230 mesh; Merck: 300 g) and eluted with a mixture of chloroform and methanol (10:1). The fractions containing the objective compound were combined and concentrated under reduced pressure to give oil. Again the oil was subjected to column chromatography on silica gel (silica gel 60, 70–230 mesh; Merck: 200 g) and eluted with a mixture of dichloromethane and acetone (5:1). The fractions containing the objective compound were combined and concentrated under reduced pressure to give 2-amino-4-methyl-5-(2-pyridylthio)thiazole (2.1 g, yield: 47.9%).

NMR (DMSO-d$_6$, 200 MHZ, ppm): 2.13 (3H, s), 6.97 (1H, m), 7.15 (1H, m), 7.28 (2H, s), 7.65 (1H, m), 8.40 (1H, m) Mass: M$^{+1}$ 224, M 223, m/e 208, 190, 181, 145, 111

EXAMPLE 66

A mixture of 2-amino-4-methyl-5-(2-pyridylthio)thiazole (1.7 g) and 3-chloroperbenzoic acid (1.8 g) in a mixture of chloroform (20 ml) and dichloromethane (50 ml) was stirred at 5° C. for 3.5 hours. The reaction mixture was washed with aqueous sodium bicarbonate and dried over magnesium sulfate. The solvent was concentrated under reduced pressure to give solid. The solid was subjected to column chromatography on silica gel (silica gel 60, 70–230 mesh; Merck: 100 g) and eluted with a mixture of chloroform and methanol (10:1). The fractions containing the objective compound were combined and concentrated under reduced pressure to give 2-amino-4-methyl-5-(2-pyridylsulfinyl)thiazole (0.95 g, yield: 52.2 %).

mp: 190°–193° C. (dec.) NMR (DMSO-d$_6$, 200 MHZ, ppm): 2.38 (3H, s), 7.50–7.58 (1H, m), 7.70 (2H, s), 7.96 (1H, d, J=8 Hz), 8.07–8.16 (1H, m), 8.6–8.63 (1H, m) Mass: M$^{+1}$ 240, M 239, m/e 223, 191, 161, 129, 111

EXAMPLE 67

A mixture of 2-acetylamino-5-bromothiazole (1.9 g), 2-mercaptoimidazole (0.9 g) and potassium carbonate (1.5 g) in N,N-dimethylformamide (30 ml) was heated at 90° C. for 2.5 hours with stirring. The reaction mixture was concentrated under reduced pressure and the residue was extracted with methanol. The solvent was concentrated under reduced pressure to give solid. The solid was subjected to column chromatography on silica gel (silica gel 60, 70–230 mesh; Merck: 150 g) and eluted with a mixture of chloroform and methanol (10:1). The fraction containing the objective compound were combined and concentrated under reduced pressure to give 2-acetylamino-5-(2-imidazolylthio)thiazole (1.8 g, yield: 87.4%).

mp: 230°–235° C. (dec.) IR (Nujol): 3150, 3100, 1710, 1550, 1290 cm$^{-1}$ NMR (DMSO-d$_6$, 200 MHZ, ppm): 2.1 (3H, s), 6.80 (1H, s), 7.08 (2H, s), 7.6 (1H, s), 12.3 (1H, s) Mass: M$^{+1}$ 241, M 240, m/e 198, 156, 100

EXAMPLE 68

A mixture of 2-acetylamino-5-(2-imidazolylthio)thiazole (1.8 g) in a mixture of concentrated hydrochloric acid (10 ml) and ethanol (50 ml) was refluxed for 5 hours with stirring. The reaction mixture was concentrated under reduced pressure and the residue was dissolved in water. The solution was adjusted to pH 8.5 using sodium bicarbonate with cooling. The precipitates were collected by filtration, washed with water and dried in vacuo to give 2-amino-5-(2-imidazolylthio)thiazole (0.35 g). The filtrate was extracted with a mixture of tetrahydrofuran and ethyl acetate (1:1), washed with aqueous saturated sodium chloride and dried over magnesium sulfate. The solvent was concentrated under reduced pressure to give solid. The solid was subjected to column chromatography on silica gel (silica gel 60, 70–230 mesh; Merck: 100 g) and eluted with a mixture of chloroform and methanol (10:1). The fractions containing the objective compound were combined and concentrated under reduced pressure give 2-amino-5-(2-imidazolylthio)thiazole (0.55 g). Total amount of 2-amino-5-(2-imidazolylthio)thiazole was 0.90 (yield: 60.4%).

mp: 209°–211° C. (dec.) IR (Nujol): 3450, 3300, 1630, 1520, 1315 cm$^{-1}$ NMR (DMSO-d$_6$, 200 MHZ, ppm): 7.05 (2H, s), 7.15 (1H, s), 7.36 (2H, s) Mass: M$^{+1}$ 199, M 198, m/e 156, 139, 100

EXAMPLE 69

A mixture of 2-acetylamino-5-bromothiazole (1.8 g), 3-hydroxy-2-mercaptopyridine (1.3 g) and potassium carbonate (2.0 g) in N,N-dimethylformamide (40 ml) was heated at 90° C. for 3.5 hours with stirring. The reaction mixture was concentrated under reduced pressure and the residue was triturated with water. The mixture was extracted with a mixture of tetrahydrofuran and ethyl acetate (1:1), washed with aqueous saturated sodium chloride and dried over magnesium sulfate. The solvent was concentrated under reduced pressure to give solid. The solid was subjected to column chromatography on silica gel (silica gel 60, 70–230 mesh; Merck: 150 g) and eluted with a mixture of chloroform and methanol (10:1). The fractions containing the objective compound were combined and concentrated under reduced pressure to give 2-acetylamino-5-(3-hydroxypyridin-2-ylthio) thiazole (2.4 g, yield: 89.9%).

mp: 236°–238° C. (dec.) IR (Nujol): 3175, 1690, 1565, 1300 cm$^{-1}$ NMR (DMSO-d$_6$, 200 MHZ, ppm): 2.16 (3H, s), 7.02–7.17 (3H, m), 7.58 (1H, s), 7.83 (1H, d, j=6 Hz), 10.70 (1H, s), 12.30 (1H, s) Mass: M$^{+1}$ 268, M 267, m/e 225, 183, 127

EXAMPLE 70

A mixture of 2-acetylamino-5-(3-hydroxypyridin-2-ylthio)thiazole (2 g) in a mixture of ethanol (40 ml), tetrahydrofuran (20 ml) and aqueous 6N-hydrochloric acid (13 ml) was refluxed for 5 hours with stirring. The reaction mixture was concentrated under reduced pressure and the residue was dissolved in water. The solution was adjusted to pH 8.5 using aqueous sodium bicarbonate and extracted with a mixture of tetrahydrofuran and ethyl acetate (1:1). The organic layer was washed with aqueous saturated sodium chloride and dried over magnesium sulfate. The solvent was concentrated under reduced pressure to give 2-amino-5-(3-hydroxypyridin-2-ylthio)thiazole (1.15 g, yield: 68.9%).

mp: 128°–130° C. IR (Nujol): 3500, 3400, 3300, 1640, 1570, 1520, 1500, 1330, 1200 cm$^{-1}$ NMR (DMSO-d$_6$, 200 MHZ, ppm): 6.97–7.11 (3H, m), 7.29 (2H, s), 7.82 (1H, d, J=6 Hz), 10.57 (1H, s) Mass: M$^{+1}$ 226, M 225, m/e 183, 139, 100

EXAMPLE 71

To a mixture of 2-amino-5-(3-hydroxylpyridin-2-ylthiothiazole (4.6 g) in a mixture of chloroform (100 ml), dichloromethane (200 ml) and N,N-dimethylformamide (50 ml) was added dropwise the solution of 3-chloroperbenzoic acid (4.3 g) in chloroform (50 ml) at 5° C. with stirring. The mixture was stirred at room temperature for 5 hours. The reaction mixture was extracted with aqueous diluted hydrochloric acid and the aqueous layer was washed with ethyl acetate. The aqueous layer was adjusted to pH 5.7 using sodium bicarbonate and extracted with a mixture of tetrahydrofuran and ethyl acetate (1:1). The organic layer was washed with aqueous saturated sodium chloride and dried over magnesium sulfate. The solvent was concentrated under reduced pressure to give solid. The solid was subjected to column chromatography on silica gel (silica gel 60, 70–230 mesh; Merck: 250 g) and eluted with a mixture of chloroform and methanol (10:1). The fractions containing the objective compound were combined and concentrated under reduced pressure to give 2-amino-5-(3-hydroxypyridin-2ylsulfinyl)thiazole (0.65 g, yield: 12.2%).

mp: 155°–158° C. (dec.) IR (Nujol): 3300, 3150, 1620, 1565, 1515, 1300 cm$^{-1}$ NMR (DMSO-d$_6$, 200 MHZ, ppm): 7.29–7.40 (2H, m), 7.59 (1H, s), 7.75 (2H, s), 8.15 (1H, br s) Mass: m/e 225, 220, 205

EXAMPLE 72

A mixture of 2-acetylamino-5-bromothiazole (1 g), 3-mercaptopyridine hydrochloride (1 g) and potassium carbonate (1.5 g) in N,N-dimethylformamide (10 ml) was heated at 90° C. for 4.5 hours with stirring. The reaction mixture was poured into ice water. The precipitates were collected by filtration, washed with water and dried in vacuo to give 2-acetylamino-5-(3-pyridylthio)thiazole (0.9 g, yield: 81.8%).

mp: 203°–205° C. (dec.) IR (Nujol): 3170, 1700, 1570, 1300 cm$^{-1}$ NMR (DMSO-d$_6$, 200 MHZ, ppm): 2.16 (3H, s), 7.33–7.39 (1H, s), 7.60 (1H, d, J=8 Hz) 7.81 (1H, s), 8.42–8.54 (2H, m), 12.45 (1H, s) Mass: M+1 252, M 251, m/e 209, 176, 167, 111

EXAMPLE 73

A mixture of 2-acetylamino-5-(3-pyridylthio)thiazole (8.5 g) in a mixture of ethanol (160 ml), tetrahydrofuran (50 ml) and aqueous 6N hydrochloric acid (100 ml) was refluxed for 4 hours with stirring. The reaction mixture was concentrated under reduced pressure and the residue was dissolved in water. The solution was adjusted to pH 8.5 using aqueous sodium bicarbonate and the precipitates were collected by filtration, washed with water and dried in vacuo to give 2-amino-5-(3-pyridylthio)thiazole (5.6 g yield: 78.9%).

mp: 140°–142° C. IR (Nujol): 3400, 3300, 3125, 11630, 1530, 1490 cm$^{-1}$ NMR (DMSO-d$_6$, 200 MHZ, ppm): 7.30 (1H, s), 7.32–7.39 (1H, m), 7.55 (2H, s), 7.57–7.61 (1H, m), 8.40 (2H, d, J=7 Hz) Mass: M$^{+1}$ 210, M 209, m/e 167, 122, 99

EXAMPLE 74

To a mixture of 2-amino-5-(3-pyridylthio)thiazole (3.0 g) in a mixture of dichloromethane (100 ml) and chloroform (100 ml) was added dropwise the solution of 3-chloroperbenzoic acid (3.4 g) in dichloromethane (50 ml) at 5° C. with stirring. The mixture was stirred at 5° C. for hours. The reaction mixture was washed with aqueous sodium bicarbonate and the aqueous layer was extracted with a mixture of tetrahydrofuran and ethyl acetate (1:1), washed with aqueous saturated sodium chloride and dried over magnesium sulfate. The solvent was concentrated under reduced pressure and the residue was recrystallized from ethanol no give 2-amino-5-(3-pyridylsulfinyl)thiazole (1.2 g, yield: 37.2%). mp: 178°–179° C. IR (Nujol): 3300, 3150, 1630, 1580, 1520, 1485, 1325, 1220 cm$^{-1}$ NMR (DMSO-d$_6$, 200 MHZ, ppm): 7.58–7.70 (1H, m), 7.80 (1H, s), 8.00 (2H, s), 7.98–8.05 (1H, m), 8.72 (2H, br s) Mass: M$^{+1}$ 226, M 225, m/e 209, 177, 147

EXAMPLE 75

A mixture of 2-amino-5-(3-pyridylsulfinyl)thiazole (1.6 g) and 3-chloroperbenzoic acid (1.8 g) in a mixture of chloroform (150 ml), dichloromethane (50 ml) and N,N-dimethylformamide (5 ml) was stirred at room temperature for 3 hours. The reaction mixture was extracted with diluted hydrochloric acid and washed with ethyl acetate. The aqueous layer was adjusted to pH 8.5 using sodium bicarbonate and the mixture was extracted with a mixture of tetrahydrofuran and ethyl acetate (1:1). The organic layer was washed with water and dried over magnesium sulfate. The solvent was concentrated under reduced pressure and the residue was triturated with ethanol to give 2-amino-5-(3-pyridylsulfonyl)thiazole (0.30 g, yield: 17.5%).

mp: 218°–220° C. (dec.) IR (Nujol): 3420, 3300, 1650, 1520, 1310 cm$^{-1}$ NMR (DMSO-d$_6$, 200 MHZ, ppm): 7.63–7.70 (1H, m), 7.78 (1H, s), 8.20 (2H, s), 8.27 (1H, d, J=8 Hz), 8.85 (1H, d, J=4 Hz), 9.06 (1H, s) Mass: M$^{+1}$ 242, M 241, m/e 177, 135, 99

EXAMPLE 76

A mixture of 2-acetylamino-5-bromothiazole (2.2 g), 2-mercapto-5-trifluoromenhylpyridine (1.9 g) and potassium carbonate (2.0 g) in N,N-dimethylformamide (40 ml) was heated at 90° C. for 4.5 hours with stirring. The reaction mixture was concentrated under reduced pressure and the residue was triturated with water. The precipitates were collected by filtration, washed with water and dried in vacuo to give 2-acetylamino-5-(5-trifluoromethylpyridin-2-ylthio) thiazole (3.2 g, yield: 100%).

mp: 165°–170° C. (dec.) IR (Nujol): 3175, 1695, 1640, 1600, 1565, 1330 cm$^{-1}$ NMR (DMSO-d$_6$, 200 MHZ, ppm): 2.19 (3H, s) 7.21 (1H, d, J=12 Hz), 7.83 (1H, s), 8.04–8.15 (1H, m), 8.18 (1H, br s), 12.53 (1H, s) Mass: M$^{+1}$ 321, M 320, M 319, m/e 277, 235, 191

EXAMPLE 77

A mixture of 2-acetylamino-5-(5-trifluoromethylpyridin-2-ylthio)thiazole (3.2 g) in a mixture of ethanol (60 ml), tetrahydrofuran (30 ml) and aqueous 6N-hydrochloric acid (10 ml) was refluxed for 3 hours with stirring. The reaction mixture was concentrated under reduced pressure and the residue was dissolved in water. The solution was adjusted to pH 8.5 using aqueous sodium bicarbonate and extracted with mixture of tetrahydrofuran and ethyl acetate (1:1) and dried over magnesium sulfate. The solvent was concentrated under reduced pressure to give solid. The solid was subjected to column chromatography on silica gel (silica gel 60, 70–230 mesh; Merck: 150 g) and eluted with a mixture of chloroform and methanol (10:1). The fractions containing the objective compound were combined and concentrated under reduced pressure to give 2-amino-5-(5-trifluoromethylpyridin-2-ylthio)thiazole (2.1 g yield: 75.8%).

mp: 135°–138° C. IR (Nujol): 3400, 3300, 3100, 1640, 1600, 1560, 1520, 1330 cm$^{-1}$ NMR (DMSO$_6$, 200 MHZ, ppm): 7.26 (1H, d, J=8 Hz), 7.33 (1H, s), 7.66 (2H, s) 7.81 (1H, d, j=8 Hz), 8.80 (1H, s) Mass: M$^{+1}$ 278, M 277, m/e 235, 191, 146, 131

EXAMPLE 78

To a solution of 2-amino-5-(5-trifluoromenhylpyridin-2-ylthio) thiazole (0.6 g) in dichloromethane (20 ml) was added portionwise 3-chloroperbenzoic acid (0.6 g) at with stirring. The mixture was stirred at 5° C. for hours. The reaction mixture was washed with aqueous sodium bicarbonate and dried over magnesium sulfate. The solvent was concentrated under reduced pressure to give solid. The solid was subjected to column chromatography on silica gel (silica gel 60, 70–230 mesh; Merck: 30 g) and eluted with a mixture of chloroform and methanol (10:1). The fractions containing the objective compound were combined and concentrated under reduced pressure to give 2-amino-5-(5-trifluoromethylpyridin-2-ylsulfinyl)thiazole (0.52 g, yield: 81.9%).

mp: 144°–145° C. NMR (DMSO-d$_6$, 200 MHZ, ppm): 7.82 (1H, s), 7.92 (2H, s), 8.21 (1H, d, J=8 Hz), 8.56 (1H, d, J=8 Hz), 9.08 (1H, s)

Mass: M 293, m/e 277, 245, 226, 179, 147

EXAMPLE 79

A mixture of 2-acetylamino-5-bromothiazole (2.2 g), 4-amino-2-mercaptopyrimidine (1.3 g) and potassium carbonate (2.0 g) in N,N-dimethylformamide (50 ml) was heated at 90° C. for 2 hours with stirring. The reaction mixture was concentrated under reduced pressure and the residue was triturated with water. The precipitation was collected by filtration, washed with water and dried in vacuo to give solid. The solid was subjected to column chromatography on silica gel (silica gel 60, 70–230 mesh; Merck: 200 g) and eluted with a mixture of chloroform and methanol (10:1). The fractions containing the objective compound were combined and concentrated under reduced pressure no give 2-acetylamino-5-(4-aminopyrimidin-2-ylthio)thiazole (1.3 g, yield: 48.7%).

mp: 255°–258° C. (dec.) IR (Nujol): 3400, 3350, 3200, 1692, 1650, 1585, 1325, 1300 cm$^{-1}$ NMR (DMSO-d$_6$, 200 MHZ, ppm): 2.16 (3H, s), 6.17 (1H, d, J=6 Hz), 7.02 (2H, s), 7.59 (1H, s), 7.85 (1H, d, J=6 Hz), 12.31 (1H, s) Mass: M$^{+1}$ 268, M 267, m/e 225, 205, 183

EXAMPLE 80

Starting from 2-acetylamino-5-bromothiazole, 2-acetylamino-5-(4-hydroxypyrimidin-2-ylthio)thiazole (0.35 g, yield: 28.8%) was obtained according to a similar manner to that of Example 67.

IR (Nujol): 3150, 1665, 1565, 1535, 1300, 1275, 1230 cm$^{-1}$ NMR (DMSO-d$_6$, 200 MHZ, ppm): 2.18 (3H, s), 6.25 (1H, d, J=6 Hz) 7.70 (1H, s), 7.93 (1H, d, J=6 Hz), 12.0–12.6 (2H, m) Mass: M$^{+1}$ 269, M 268, m/e 259, 197, 135

EXAMPLE 81

A mixture of 2-acetylamino-5-(4-hydroxypyrimidin-2-ylthio)thiazole (3.7 g) in a mixture of ethanol (100 mi), tetrahydrofuran (40 ml) and aqueous 6N-hydrochloric acid (20 ml) was refluxed for 6.5 hours with stirring. The reaction mixture was concentrated under reduced pressure and the residue was dissolved in water. The solution was adjusted to pH 8.5 using aqueous sodium bicarbonate. The precipitates were collected by filtration, washed with water and dried in vacuo to give solid. The solid was subjected to column chromatography on silica gel (silica gel 60, 70–230 mesh; Merck: 250 g) and eluted with a mixture of chloroform and methanol (10:1). The fractions containing the objective compound were combined and concentrated under reduced pressure to give 2-amino-5-(4-hydroxpyrimidin-2-ylthio) thiazole (0.45 g, yield: 14.5%).

mp: 210°–220° C. (dec.) IR (Nujol): 3450, 3350, 3125, 1675, 1510, 1230 cm$^{-1}$ NMR (DMSO-d$_6$, 200 MHZ, ppm): 5.45 (1H, d, J=7 Hz), 7.30–7.40 (3H, m), 7.64 (1H, m) Mass: m/e 220, 205, 132, 112

EXAMPLE 82

Starting from 2-acetylamino-5-bromothiazole, 2-acetylamino-5- (4-methylpyrimidin-2-ylthio) thiazole (2.89 g, yield: 48.0%) was obtained according to a similar manner to that of Example 67.

mp: 210° C. (dec.) IR (Nujol): 3170, 1720, 1695, 1575, 1555, 1335 cm$^{-1}$ NMR (DMSO-d$_6$, 200 MHZ, ppm): 2.19 (3H, s), 2.19 (3H, s), 7.16 (1H, d, J=5 Hz), 7.70 (1H, s), 8.46 (1H, d, J=5 Hz), 12.38 (1H, s) Mass: M$^{+2}$ 268, M$^{+1}$ 267, M 266, m/e 224, 182, 165

EXAMPLE 83

Starting from 2-acetylamino-5-(4-methylpyrimidin-ylthio)thiazole, 2-amino-5-(4-methylpyrimidin-2-ylthio)thiazole (0.40 g, yield: 16.4%) was obtained according to a similar manner to that of Example 58.

mp: 158°–159° C. IR (Nujol): 3430, 3280, 3100, 1620, 1565, 1520, 1490, 1330, 1210 cm$^{-1}$ NMR (DMSO-d$_6$, 200 MHZ, ppm): 2.39 (3H, s), 7.14 (1H, d, J=5 Hz), 7.15 (1H, s), 7.43 (2H, s), 8.47 (1H, d, J=5 Hz) Mass: M$^{+2}$ 226, M$^{+1}$ 225, M 224, m/e 182, 138 Analysis Calcd. for C$_8$H$_8$N$_4$S$_2$C 42.84, H 3.59, N 24.99 Found: C 42.81, H 3.50, N 24.86

EXAMPLE 84

To a solution of 2-amino-5-(2-pyrimidinylthio)-thiazole (1.0 g) in a pyridine (20 ml) was dropwise added methanesulfonyl.chloride (0.8 ml) at 5° C. with stirring. The mixture was stirred at room temperature for 24 hours. The reaction mixture was concentrated under reduced pressure and water was added to this residue. The mixture was extracted with a mixture of tetrahydrofuran and ethyl acetate (1:1), washed with aqueous saturated sodium chloride and dried over magnesium sulfate. The solution was concentrated under reduced pressure to give solid. The solid was recrystallized from 50% ethanol to give 2-methanesulfonylamino-5-(2-pyrimidinylthio)thiazole (0.60 g, yield: 43.8%).

mp: 200° C. (dec.) IR (Nujol): 3120, 1585, 1545, 1440, 1305, 1140 cm$^{-1}$ NMR (DMSO-d$_6$, 200 MHZ, ppm): 2.98 (3H, s), 7.35 (1H, t, d=7 Hz), 7.76 (1H, s), 8.71 (2H, d, j=7 Hz), 12.89 (1H, br s) Mass: M$^{+2}$ 290, M$^{+1}$ 289, M 288, m/e 209, 168 Analysis Calcd. for C$_8$H$_8$N$_4$O$_2$S$_3$ C 33.32, H 2.80, N 19.43 Found: C 33.04, H 2.74, N 19.06

EXAMPLE 85

Starting from 2-amino-5-(2-pyrimidinylthio)thiazole, 2-amino-5-(2-pyrimidinylsulfinyl)thiazole (0.52 g, yield: 32.2%) was obtained according to a similar manner to that of Example 66.

mp: 206° (dec.) IR (Nujol): 3300, 3200, 1615, 1565, 1545, 1520, 1230, 1150 cm$^{-1}$ NMR (DMSO-d$_6$, 200 MHZ, ppm): 7.67 (1H, t, J=5 Hz) 7.73 (1H: s), 7.87 (2H, s), 8.99 (2H, d, j=8 Hz) Mass: M 226, m/e 210, 178, 168, 147 Analysis Calcd. for C$_7$H$_6$N$_4$OS$_2$ C37.16, H 2.67, N 24.76 Found : C 36.78, H 2.62, N 24.62

EXAMPLE 86

Starting from 2-amino-5-(2-pyrimidinylthio)thiazole, 2-amino-5-(2-pyrimidinylsulfonyl)thiazole (0.464 g, yield: 8.1%) was obtained according to a similar manner to that of Example 75.

mp: 214° C. (dec.) IR (Nujol): 3400, 3100, 1615, 1570, 1515, 1335, 1210, 1140 cm$^{-1}$ NMR (DMSO-d$_6$, 200 MHZ, ppm): 7.73 (1H, s), 7.80 (1H, t, d=5 Hz), 8.23 (2H, s), 9.05 (2H, d, J=5 Hz) Mass: M$^{+2}$ 244, M 243, M 242, m/e 178, 136

What we claim is:

1. A compound of the formula:

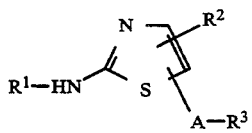

wherein
R$^1$ is hydrogen or acyl which may be substituted with halogen,
R$^2$ is hydrogen, lower alkyl, hydroxy(lower)alkyl, halogen or carboxy,
A is

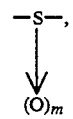

wherein m is 0, 1, or 2, and
R$^3$ is an unsaturated heterocyclic group selected from the group consisting of pyrrolyl, pyrrolinyl, imidazolyl, pyrazolyl, pyrimidinyl, pyrazinyl, pyridazinyl, triazolyl, tetrazolyl, and thiadiazolyl;
wherein said unsaturated heterocyclic group may be substituted 1 to 4 times with lower alkyl, amino, hydroxy, or halo(lower)alkyl, or pharmaceutically acceptable salts thereof.

2. A compound of the formula:

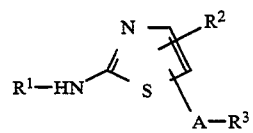

wherein
R$^1$ is lower alkanesulfonyl which may be substituted with halogen,
R$^2$ is hydrogen, lower alkyl, hydroxy(lower)alkyl, halogen or carboxy,
A is

wherein m is 0, 1 or 2, and
R$^3$ is an unsaturated heterocyclic group selected from the group consisting of pyrrolyl, pyrrolinyl, imidazolyl, pyrazolyl, pyrimidinyl, pyrazinyl, pyridazinyl, triazolyl, tetrazolyl and thiadiazolyl;
wherein said unsaturated heterocyclic group may be substituted 1 to 4 times with lower alkyl, amino, hydroxy, or halo(lower)alkyl,
or pharmaceutically acceptable salts thereof.

3. A pharmaceutical composition which comprises, as an active ingredient, a compound of claim 1 or 2 or a pharmaceutically acceptable salt thereof in admixture with pharmaceutically acceptable carriers.

4. The compound of claim 1, wherein R$^1$ is hydrogen, lower alkanoyl or benzoyl which may be substituted with halogen.

* * * * *